(12) United States Patent
Hwang et al.

(10) Patent No.: US 11,041,854 B2
(45) Date of Patent: Jun. 22, 2021

(54) BIOSENSOR USING MAGNETIC NANOPARTICLES, AND DETECTION DEVICE AND DETECTION METHOD USING SAME

(71) Applicant: BBC INC., Gyeonggi-do (KR)

(72) Inventors: Hyundoo Hwang, Seoul (KR); Jaekyu Choi, Seoul (KR)

(73) Assignee: BBB INC., Seongnam-si (KR)

( * ) Notice: Subject to any disclaimer, the term of this patent is extended or adjusted under 35 U.S.C. 154(b) by 0 days.

(21) Appl. No.: 17/002,632

(22) Filed: Aug. 25, 2020

(65) Prior Publication Data

US 2021/0033603 A1    Feb. 4, 2021

Related U.S. Application Data

(63) Continuation of application No. PCT/KR2018/009115, filed on Aug. 9, 2018.

(51) Int. Cl.
*G01N 33/543*    (2006.01)
*G01N 27/327*    (2006.01)
*G01N 33/553*    (2006.01)

(52) U.S. Cl.
CPC ... *G01N 33/54333* (2013.01); *G01N 27/3277* (2013.01); *G01N 27/3278* (2013.01);
(Continued)

(58) Field of Classification Search
CPC ......... G01N 33/54333; G01N 27/3278; G01N 33/54393; G01N 27/3277; G01N 33/5438
See application file for complete search history.

(56) References Cited

U.S. PATENT DOCUMENTS

2005/0053962 A1\*  3/2005  Blackburn ............. B82Y 30/00
                                                435/6.11
2014/0272945 A1    9/2014  Kim et al.
2018/0318834 A1\*  11/2018  Fomina .............. C12N 15/1003

FOREIGN PATENT DOCUMENTS

KR    10-2008-0091955 A    10/2008
KR    10-2013-0040715 A     4/2013
(Continued)

OTHER PUBLICATIONS

Chung et al. "Magnetic force assisted electrochemical sensor for the detection of thrombin with aptamer-antibody sandwich formation." Biosensors and Bioelectronics. vol. 117, Oct. 15, 2018, pp. 480-486.
(Continued)

*Primary Examiner* — Sally A Merkling
(74) *Attorney, Agent, or Firm* — Knobbe Martens Olson & Bear LLP

(57) ABSTRACT

According to one embodiment of the present application, a biosensor, the biosensor comprising: a reaction part including a magnetic nanoparticle complex, a first electrode, and a second electrode; and a sample introduction part forming a passage so that a sample can be introduced into the reaction part from an outside of the biosensor; wherein the magnetic nanoparticle complex includes a first capturing substance for capturing a first target substance, a magnetic nanoparticle, and a reaction substance that performs at least one of an oxidation reaction and a reduction reaction, wherein the magnetic nanoparticle complex has is magnetic in the reaction part, and has a property that mobility can be changed according to a change in a condition of the reaction part, wherein the first electrode, a second capturing substance for capturing a second target substance is fixed, wherein the second electrode is an electrode different from the first electrode, and characterized in that at least one of the
(Continued)

first target substance and the second target substance is included in the sample, may be provided.

17 Claims, 16 Drawing Sheets

(52) U.S. Cl.
CPC ... *G01N 33/5438* (2013.01); *G01N 33/54346* (2013.01); *G01N 33/54393* (2013.01); *G01N 33/553* (2013.01)

(56) References Cited

FOREIGN PATENT DOCUMENTS

| KR | 10-2014-0102568 A | 8/2014 |
|----|-------------------|--------|
| KR | 10-2015-0064927 A | 6/2015 |
| KR | 10-1880862 B1     | 7/2018 |

OTHER PUBLICATIONS

Grant of Patent for Korean Application No. 10-2018-7023834 dated Apr. 18, 2020.
Hwang et al. "mark B: A Novel Point-of-Care Immunoassay Platform for Quantification of Blood Biomarkers." The 70$^{th}$ AACC Annual Scientific Meeting & Clinical Lab Expo, Jul. 29-Aug. 2, 2018, Chicago, IL.
International Search Report for International Application No. PCT/KR2018/009115 dated Apr. 29, 2019.
Notification of Reason for Refusal for Korean Application No. 10-2018-7023834 dated Jan. 15, 2020.

* cited by examiner

BIOSENSOR USING MAGNETIC NANOPARTICLES, AND DETECTION DEVICE AND DETECTION METHOD USING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

Embodiments relate to a biosensor using magnetic nanoparticles.

Embodiments relate to a detection device using the biosensor.

Embodiments relate to a detection method of the detection device using the biosensor.

Description of the Related Art

With the advent of an aging society, as the demand for point-of-care testing (POCT) for disease prevention and early diagnosis has increased, various on-site diagnostic kits such as biosensors using membranes and biosensors using micro fluidic channels have been commercialized. The demand for these products is also increasing rapidly.

However, when compared with the disease diagnosis accuracy and sensitivity of an enzyme-linked immunospecific assay (ELISA) method conducted by a person in a clinical trial room of a large hospital, there is a problem in that accuracy and sensitivity of disease diagnosis of the various on-site diagnostic kits have been significantly degraded.

One among causes degrading the accuracy and sensitivity of the disease diagnosis is that backgrounds of a sample and the like degrade detection accuracy. This remains as a chronic problem because it is difficult to remove the backgrounds without additional and costly device design or human washing due to the nature of the biosensor in which movement and reaction of a sample are performed by a capillary force without provision of an extra external force.

Thus, there is a need for a part for washing unnecessary reactants on an on-site diagnostic kit through a simple method to remove a background and improve detection accuracy and detection sensitivity.

SUMMARY

Technical Problem

Embodiments are directed to providing a biosensor for solving a problem in that accuracy is degraded due to a background.

Embodiments are also directed to providing a biosensor with improved detection sensitivity by stabilizing a detected signal.

Technical Solution

According to one embodiment of the present application, a biosensor, the biosensor comprising: a reaction part including a magnetic nanoparticle complex, a first electrode, and a second electrode; and a sample introduction part forming a passage so that a sample can be introduced into the reaction part from an outside of the biosensor; wherein the magnetic nanoparticle complex includes a first capturing substance for capturing a first target substance, a magnetic nanoparticle, and a reaction substance that performs at least one of an oxidation reaction and a reduction reaction, wherein the magnetic nanoparticle complex is magnetic in the reaction part, and has a property that mobility can be changed according to a change in a condition of the reaction part, wherein the first electrode, a second capturing substance for capturing a second target substance is fixed, wherein the second electrode is an electrode different from the first electrode, and characterized in that at least one of the first target substance and the second target substance is included in the sample, may be provided.

According to one embodiment of the present application, a detection device, the detection device comprising: an electrode part capable of being connected to a biosensor, wherein the biosensor includes a magnetic nanoparticle complex including a first capturing substance for capturing a first target substance, a magnetic nanoparticle and a reaction substance that performs at least one of an oxidation reaction and a reduction reaction, a first electrode to which the second target substance for capturing a second target substance is fixed, and a second electrode different with the first electrode, and wherein at least one of the first target substance and the second target substance are included in a sample, and a control unit for controlling to provide a voltage including a first step of raising the voltage applied between the first electrode and the second electrode and a second step of falling the voltage, in order to detect whether the second target substance is captured in the sample introduced into the biosensor by detecting a current according to a change in the applied voltage, and to provide a voltage that applies a voltage higher than a minimum voltage of at least one of the lowest voltage in the first step and the lowest voltage in the second step for a predetermined time or longer, in order to stabilize the curve of the current, before providing a voltage to include the first step and the second step, may be provided.

Advantageous Effects

According to embodiments, it is possible to provide a biosensor which solves a problem in that accuracy is degraded due to a background, through washing performed by changing an environmental condition in a reaction part.

According to the embodiments, it is possible to provide a biosensor with improved detection sensitivity by providing a voltage for stabilizing a signal prior to a detection operation.

The effects of the present application are not limited to the above-described effects, and effects not mentioned will be apparently understood by those skilled in the art from the present specification and the accompanying drawings.

DETAILED DESCRIPTION

Modes of the Invention

Figure 1:
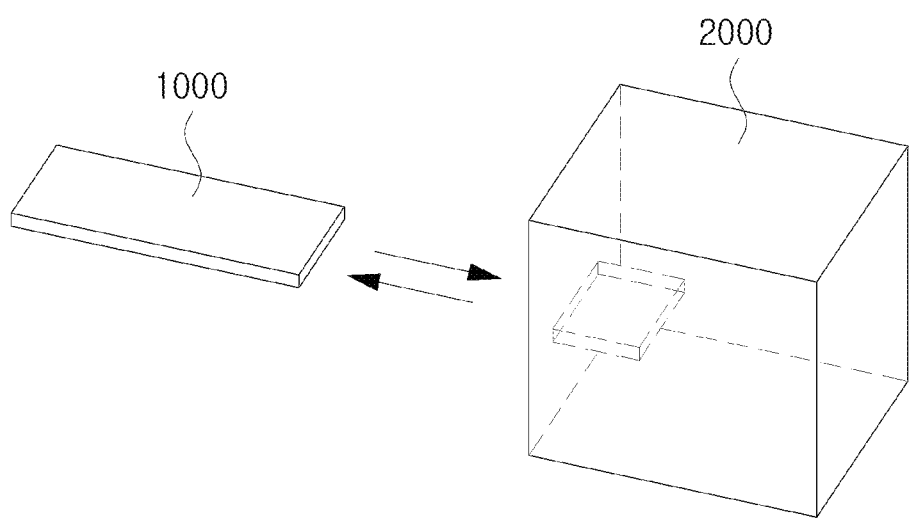
FIG. 1 is a diagram for describing a detection system (1) according to one embodiment of the present application.

The above-described purposes, features and advantages of the present application will become more apparent through the following detailed description in connection with the accompanying drawings. However, the present application may be modified in various ways and may have various embodiments. Hereinafter, specific embodiments will be illustrated in the drawings and described in detail.

In the drawings, the thickness of the layers and regions are exaggerated for clarity. What an element or layer is referred to as "on" or "on" of another component or layer is not only directly above the other component or layer, but also another layer or other component in the middle. Therefore, the meaning of "on" includes both of the case. Throughout the specification, the same reference numbers refer to the same components in principle. In addition, elements having the same functions within the scope of the same idea appearing in the drawings of the respective embodiments will be described using the same reference numerals.

If it is determined that a detailed description of known functions or configurations related to the present application may unnecessarily obscure the subject matter of the present application, the detailed description will be omitted. In addition, the numbers used in the description process of the present specification (eg, first, second, etc.) are merely identification symbols for distinguishing one component from other components.

In addition, the suffixes "module" and "part" for components used in the following description are given or mixed only considering the ease of writing the specification, and do not have a meaning or a role that is distinguished from each other.

According to one embodiment of the present application, a biosensor, the biosensor comprising: a reaction part including a magnetic nanoparticle complex, a first electrode, and a second electrode; and a sample introduction part forming a passage so that a sample can be introduced into the reaction part from an outside of the biosensor; wherein the magnetic nanoparticle complex includes a first capturing substance for capturing a first target substance, a magnetic nanoparticle, and a reaction substance that performs at least one of an oxidation reaction and a reduction reaction, wherein the magnetic nanoparticle complex has is magnetic in the reaction part, and has a property that mobility can be changed according to a change in a condition of the reaction part, wherein the first electrode, a second capturing substance for capturing a second target substance is fixed, wherein the second electrode is an electrode different from the first electrode, and characterized in that at least one of the first target substance and the second target substance is included in the sample, may be provided.

A biosensor, wherein the magnetic nanoparticle is modified to expose a reactor to an outside of the magnetic nanoparticle, characterized in that the reaction substance is fixed to the reactor, may be provided.

A biosensor, wherein the biosensor characterized in that the reactor is an amine, and the reaction substance is gold, may be provided.

A biosensor, wherein the biosensor characterized in that the first capturing substance is fixed to the reaction substance fixed to the reactor, may be provided.

A biosensor, wherein a blocking substance that prevents adsorption of the second target substance is disposed in at least a portion of the first electrode, may be provided.

A biosensor, wherein the biosensor characterized in that the blocking substance is a BSA (Bovine Serum Albumin), may be provided.

A biosensor, wherein the first capturing substance includes at least one of an antigen, an antibody, a modified antibody, an antibody analog, an aptamer, a nucleic acid, a lipid, and a viral protein antigen, and wherein the second capturing substance includes at least one of the antigen, the antibody, the modified antibody, the antibody analog, the aptamer, the nucleic acid, the lipid, and the viral protein antigen, may be provided.

A biosensor, wherein the first target substance is same substance with the second target substance included in the sample, and wherein the first capturing substance is same substance with the second capturing substance, may be provided.

A biosensor, wherein the first target substance is the second target substance fixed on the first electrode, wherein the second target substance is the same substance with the first capturing substance, and characterized in that the first capturing substance is included in the sample, may be provided.

A biosensor, wherein the first target substance is the second target substance fixed on the first electrode, wherein the second target substance is the same substance with the first capturing substance, and characterized in that the second capturing substance is included in the sample, may be provided.

A biosensor, when a magnetic field formed in the reaction part, wherein a direction of a movement of the magnetic nanoparticle complex is changed, may be provided A biosensor, when a voltage applied between the first electrode and the second electrode is changed, wherein a direction of a movement of the magnetic nanoparticle complex is changed, may be provided.

A biosensor, wherein the biosensor further comprising a third electrode having a coil shape different from the first electrode and the second electrode, and when a current applied to the third electrode is changed, wherein a direction of a movement of the magnetic nanoparticle complex is changed, may be provided.

A biosensor, wherein the biosensor, at least a portion of a fourth electrode electrically connected to the first electrode and at least a portion of a fifth electrode electrically connected to the second electrode are exposed to the outside of the biosensor, may be provided.

A biosensor, wherein the first electrode and the fourth electrode are composed of one electrode, and wherein the second electrode and the fifth electrode are composed of one electrode, may be provided.

A biosensor, wherein at least a portion of fourth electrode and at least a portion of fifth electrode are electrically connected to a device capable of measuring a current, may be provided A biosensor, wherein a voltage applied between the first electrode and the second electrode is controlled by the device, wherein, according to current by applying the voltage between the first electrode and the second electrode, capable of detecting whether the second target substance is included in the sample, may be provided.

According to one embodiment of the present application, a detection device, the detection device comprising: an electrode part capable of being connected to a biosensor, wherein the biosensor includes a magnetic nanoparticle complex including a first capturing substance for capturing a first target substance, a magnetic nanoparticle and a reaction substance that performs at least one of an oxidation reaction and a reduction reaction, a first electrode to which the second target substance for capturing a second target substance is fixed, and a second electrode different with the first electrode, and wherein at least one of the first target substance and the second target substance are included in a sample, and a control unit for controlling to provide a voltage including a first step of raising the voltage applied between the first electrode and the second electrode and a second step of falling the voltage, in order to detect whether the second target substance is captured in the sample introduced into the biosensor by detecting a current according to a change in the applied voltage, and to provide a voltage that applies a voltage higher than a minimum voltage of at least one of the lowest voltage in the first step and the lowest voltage in the second step for a predetermined time or longer, in order to stabilize the curve of the current, before providing a voltage to include the first step and the second step, may be provided.

A detection device, wherein the first capturing substance includes at least one of an antigen, an antibody, a modified antibody, an antibody analog, an aptamer, a nucleic acid, a lipid, and a viral protein antigen, and wherein the second capturing substance includes at least one of the antigen, the antibody, the modified antibody, the antibody analog, the aptamer, the nucleic acid, the lipid, and the viral protein antigen, may be provided.

A detection device, wherein the first capturing substance is same substance with the second capturing substance, wherein the first target substance is same substance with the second target substance, and wherein the first target substance is including in the sample, may be provided.

A detection device, wherein the control unit controls to provide the voltage that the voltage between the first electrode and the second electrode is raised from at least 0 V to at least 1 V, in the first step, and controls to provide the voltage that the voltage between the first electrode and the second electrode is fallen from at least 1 V to at least 0 V, in the second step, may be provided.

A detection device, wherein the control unit controls to provide the voltage applied by the voltage of at least 1 V for at least 2 seconds between the first electrode and the second electrode, in order to stabilize the curve of the current, may be provided.

A detection device, wherein the control unit, for stabilizing the curve of the current, after controlling to provide the voltage applied by the voltage of at least 1 V for at least 2 seconds between the first electrode and the second electrode, controls to provide the voltage that the voltage between the first electrode and the second electrode is fallen from at least 1 V or more to at least 0 V or less, may be provided.

A detection device, wherein the control unit, for stabilizing the curve of the current, after controlling to provide the voltage that the voltage between the first electrode and the second electrode is fallen from at least 1 V or more to at least 0 V or less, controls to provide the voltage that the voltage between the first electrode and the second electrode is raised from at least 0 V or less to at least 1 V or more, may be provided.

A detection device, wherein the control unit, for stabilizing the curve of the current, after controlling to provide the voltage applied by the voltage of at least 1 V for at least 2 seconds between the first electrode and the second electrode, controls to provide the voltage that the voltage between the first electrode and the second electrode is raised from at least 0 V or less to at least 1 V or more, may be provided.

According to one embodiment of the present application, a detection method of a detection device electrically connected to a biosensor including a magnetic nanoparticle complex including a first capturing substance for capturing a first target substance, a magnetic nanoparticle and a reaction substance that performs at least one of an oxidation reaction and a reduction reaction, a first electrode to which the second target substance for capturing a second target substance is fixed, and a second electrode different with the first electrode, wherein at least one of the first target substance and the second target substance is included in a sample, the detection method comprising: providing a circulating voltage including a first step of raising a voltage applied between the first electrode and the second electrode and a second step of falling the voltage applied between the first electrode and the second electrode, in order to detect whether the second target substance in the sample introduced into the biosensor is captured by detecting a current according to a change in the applied voltage; before a step of providing the voltage, stabilizing a signal for applying the voltage higher than at least one of a minimum voltage of the first step and the minimum voltage of the second step for a predetermined period or more to stabilize the curve of the current; and detecting the current according to the first step and the current according to the second step, may be provided.

A detection method, wherein the first capturing substance includes at least one of an antigen, an antibody, a modified antibody, an antibody analog, an aptamer, a nucleic acid, a lipid, and a viral protein antigen, and wherein the second capturing substance includes at least one of the antigen, the antibody, the modified antibody, the antibody analog, the aptamer, the nucleic acid, the lipid, and the viral protein antigen, may be provided.

A detection method, wherein the first capturing substance is same substance with the second capturing substance, wherein the first target substance is same substance with the second target substance, characterized in that wherein the first target substance is including in the sample, may be provided.

A detection method, wherein the first step is a step in which the voltage between the first electrode and the second electrode is raised from at least 0 V to at least 1 V, and wherein the second step is a step in which the voltage between the first electrode and the second electrode is fallen from at least 1 V to at least 0 V, may be provided.

A detection method, wherein the step of stabilizing the signal is, wherein the step of stabilizing the signal for applying the voltage higher than at least one of the minimum voltage of the first step and the minimum voltage of the second step for the predetermined period or more further comprising: providing the voltage such that the voltage of at least 1V is applied between the first electrode and the second electrode for at least 2 seconds, may be provided.

A detection method, wherein the step of stabilizing the signal is further comprising, after providing the voltage such that the voltage of at least 1V is applied between the first electrode and the second electrode for at least 2 seconds, providing the voltage such that the voltage between the first electrode and the second electrode is fallen from at least 1V or more to at least 0V or less, may be provided.

A detection method, wherein the step of stabilizing the signal is further comprising, after providing the voltage such that the voltage between the first electrode and the second electrode is fallen from at least 1V or more to at least 0V or less, providing the voltage such that the voltage between the first electrode and the second electrode is raised from at least 0V or less to at least 1V or more, may be provided.

A detection method, wherein the step of stabilizing the signal is further comprising, after providing the voltage such that the voltage of at least 1V is applied between the first electrode and the second electrode for at least 2 seconds, providing the voltage such that the voltage between the first electrode and the second electrode is raised from at least 0V or less to at least 1V or more, may be provided.

Detection System 1

Hereinafter, a detection system 1 capable of detecting whether a target substance is present in a sample will be described.

For example, the detection system 1 will be disclosed which is capable of detecting whether a target disease (that is, a disease to be confirmed) is present in a sample such as blood, urine, a deoxyribonucleic acid (DNA) sample, or the like, which may be extracted from a human body, on the basis of the presence or absence of a specific antigen, an antibody, DNA, and/or ribonucleic acid (RNA) (that is, the presence or absence of a target substance).

FIG. 1 is a diagram for describing a detection system 1 according to one embodiment of the present application.

According to one embodiment of the present application, the detection system 1 may include a biosensor 1000 and a detection device 2000.

The biosensor 1000 may include a biological receptor capable of being induced a specific reaction with a target substance contained in a sample. The biosensor 1000 may be a device manufactured to detect the presence or absence of the target substance in a sample, either alone or through the detection device 2000, involved in converting such the above specific reaction into an electrical or optical signal.

For example, the biosensor 1000 may be a micro fluid dynamics-based biosensor 1000 which is designed to allow a sample to move in a micro fluidic channel due to an influence of surface tension of a fluid. In this case, the biosensor 1000 may be made of a material having rigidity. For example, the biosensor 1000 may include plastic and/or glass.

The biosensor 1000 according to one embodiment of the present application will be described in more detail below.

The detection device 2000 may be a device for detecting a variation in an electrical, optical, magnetic, and/or thermal signal which is derived from a result according to a reaction in the biosensor 1000 and determining the presence or absence of the target substance in the sample.

For example, the detection device 2000 may include an input port into which the biosensor 1000 is input and determine whether a target substance is present in a sample introduced into the biosensor 1000 on the basis of an electrical variation of the biosensor 1000.

The detection device 2000 may be a single device manufactured to detect a result value depending on the biosensor 1000 or may be a device having other functions modified to detect the result value depending on the biosensor 1000. For example, the detection device 2000 may be a detection device 2000 for the biosensor 1000, a mobile phone device of which one region is modified to allow the biosensor 1000 to be input, or a device implemented in the form of being integrated with a household appliance.

In addition, the present application is not limited to the above-described example, and any detection device 2000 easily derived from the disclosure of the detection device 2000, which will be described below, according to one embodiment of the present application, may correspond to the detection device 2000 according to the present application.

Biosensor 1000

1. Configuration of Biosensor 1000

Figure 2:
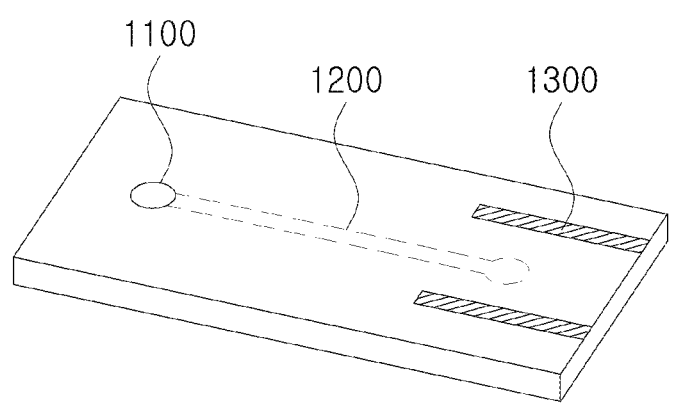
FIG. 2 is a diagram for describing a biosensor (1000) according to one embodiment of the present application.

FIG. 2 is a diagram for describing a biosensor 1000 according to one embodiment of the present application.

The biosensor 1000 may include a sample introduction part 1100, a reaction part 1200, and/or a contact part 1300. However, all the above components need not be included, and each component may be omitted or duplicated, and a biosensor 1000 may also be manufactured in the form of further including components in addition to the above disclosed components.

1.1 Sample Introduction Part 1100

The sample introduction part 1100 may be a region in which a sample is introduced from the outside to the inside of the biosensor 1000. In other words, the sample introduction part 1100 may be a region forming a channel which allows the sample to be introduced into the reaction part 1200 which will be described below.

The sample may be a matter including a target substance. For example, the sample may be a secretion secreted from a living body. The sample may be blood, plasma, serum, saliva, urine, or the like. As another example, the sample may be a material obtained for a research purpose. The sample may be a DNA sample, an RNA sample, or the like obtained from an incident site or a DNA sample, an RNA sample, or the like extracted from an animal cell or a virus.

The sample provided to the sample introduction part 1100 may move in the interior of the biosensor 1000. The sample provided to the sample introduction part 1100 may move from the sample introduction part 1100 to the reaction part 1200.

The sample may move along a micro channel. The sample may move on a membrane. In addition to the above description, the sample provided through the sample introduction part 1100 may move according to a movement method implemented through various manners utilized in the biosensor 1000.

1.2 Reaction Part 1200

The reaction part 1200 may be a region in which a specific reaction is performed. The reaction part 1200 may be a region in which a specific reaction is performed between a target substance and a capturing substance for capturing the target substance in the biosensor 1000.

The target substance may be a material to be detected that is included in the sample. For example, the target substance may be an antigen. In other words, the target substance may be an antigen related to a disease detected in blood or the like of a patient with a disease. As another example, the target substance may be DNA. In other words, the target substance may be DNA of a virus detected in blood or the like of a patient with a disease.

The capturing substance may be a material which is specifically bound with the target substance. For example, the capturing substance may be an antibody. The capturing substance may be an antibody which is specifically bound with the antigen on the basis of an antigen-antibody reaction. As another example, the capturing substance may be DNA. The capturing substance may be DNA which is specifically bound with the DNA on the basis of complementarity of a specific sequence.

Figure 3:
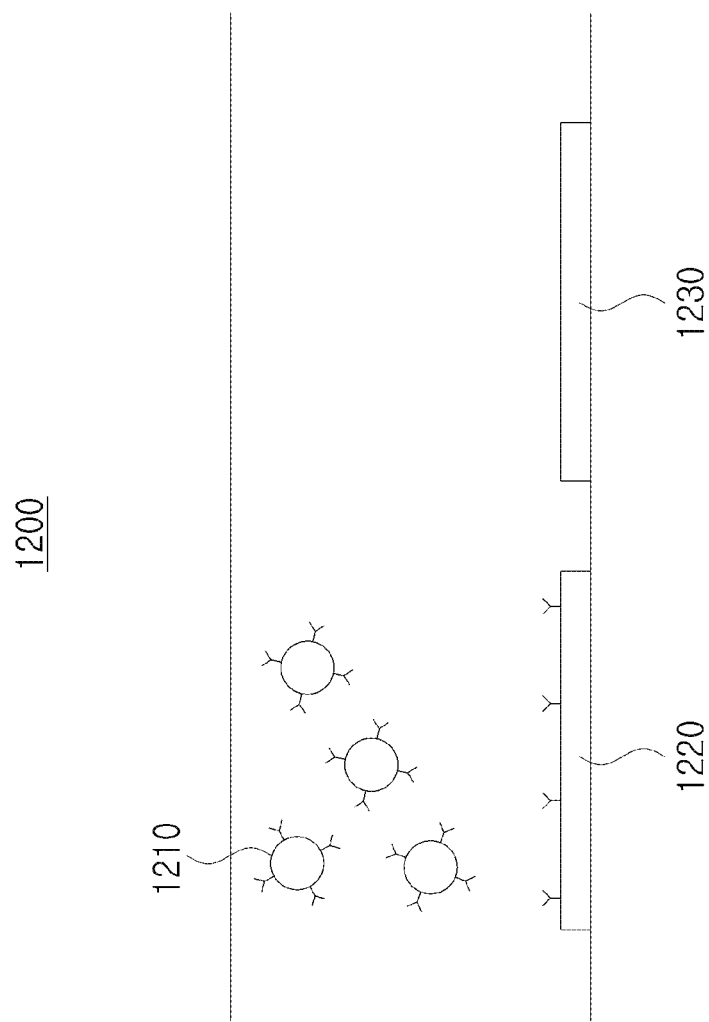
FIG. 3 is a diagram for describing a reaction part (1200) according to one embodiment of the present application.

FIG. 3 is a diagram for describing a reaction part 1200 according to one embodiment of the present application.

The reaction part 1200 may include a magnetic nanoparticle complex 1210, a first electrode 1220, and/or a second electrode 1230. However, all the above components need not be included, and each component may be omitted or duplicated, and a biosensor 1000 may also be manufactured to include the reaction part 1200 in the form of further including components in addition to the above disclosed components.

The first electrode 1220 may be disposed upstream from the second electrode 1230. Here, the term "upstream" may mean that the sample is disposed at an upstream based on a movement direction from a position introduced through the sample introduction part 1100 to the reaction part 1200. In this case, the first electrode 1220 may be closer to the sample introduction part 1100 than the second electrode 1230.

Alternatively, the first electrode 1220 may be disposed downstream from the second electrode 1230. Here, the term "downstream" may mean that the sample is disposed at a downstream based on the movement direction from the position introduced through the sample introduction part 1100 to the reaction part 1200. In this case, the second electrode 1230 may be closer to the sample introduction part 1100 than the first electrode 1220.

Alternatively, the first electrode 1220 and the second electrode 1230 may be disposed to face each other. The first electrode 1220 and the second electrode 1230 may have the same distance from the sample introduction part 1100.

The magnetic nanoparticle complex 1210 may be disposed upstream from the first electrode 1220. The magnetic nanoparticle complex 1210 may be disposed upstream from the second electrode 1230. The magnetic nanoparticle complex 1210 may be disposed upstream from the first electrode 1220 and the second electrode 1230.

Hereinafter, each component will be described in more detail.

1.2.1 Magnetic Nanoparticle Complex 1210

1.2.1.1 Meaning

Figure 4:
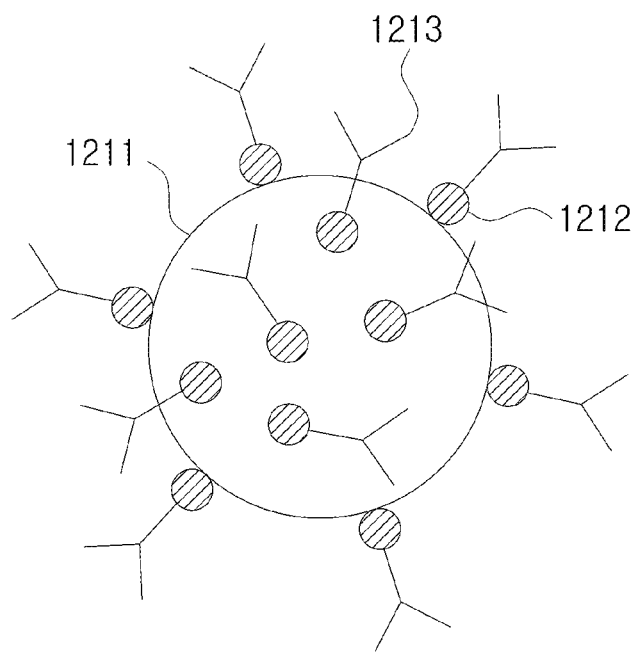
FIG. 4 is a diagram for describing a magnetic nanoparticle complex (1210) according to one embodiment of the present application.

FIG. 4 is a diagram for describing a magnetic nanoparticle complex 1210 according to one embodiment of the present application.

The magnetic nanoparticle complex 1210 may include a magnetic nanoparticle 1211, reaction substances 1212, and/or first capturing substances 1213. However, all the above components need not be included, and each component may be omitted or duplicated, and a magnetic nanoparticle complex 1210 may also be provided in the form of further including components in addition to the above disclosed components.

The magnetic nanoparticle 1211 is a magnetic particle. Types of the magnetic nanoparticle 1211 may include iron oxide ($Fe_2O_3$ or $Fe_3O_4$), ferrite (having a form in which one Fe is changed from $Fe_3O_4$ into another magnetically related atom, for example, $CoFe_2O_4$ or $MnFe_2O_4$)), and/or an alloy (alloys with precious metals to solve an oxidation problem caused due to magnetic atoms and increase conductivity and stability, for example, FePt, CoPt, and the like). For example, the magnetic nanoparticle 1211 may be a $Fe_2O_3$ particle having a size ranging from 200 nm to 500 nm and having a ferromagnetic property.

The reaction substance 1212 may be a material for performing at least one of an oxidation reaction and a reduction reaction. The reaction substance 1212 is a material having high thermal conductivity and electrical conductivity and may include a transition metal, a post-transition metal, and/or a metalloid. For example, the reaction substance 1212 may mean a gold (Au) particle. Alternatively, the reaction substance 1212 may mean a silver (Ag) particle.

The reaction substance 1212 may be fixed to the magnetic nanoparticle 1211. For example, the reaction substance 1212 may be fixed to the magnetic nanoparticle 1211 through a chemical bonding force with the magnetic nanoparticle 1211. Alternatively, the reaction substance 1212 may fixed to the magnetic nanoparticle 1211 by binding an amine group exposed to the outside of the magnetic nanoparticle 1211.

The first capturing substance 1213 may be a material which is specifically bound with a first target substance. For example, the first target substance may be a target substance (that is, a material to be detected, which is included in a sample). In this case, the first capturing substance 1213 may be a material which is specifically bound with the target substance. Alternatively, the first target substance may be a material which is specifically bound with the target substance. In this case, the first capturing substance 1213 may specifically bond to a material which is specifically competitively bound with the target substance, competitively with the target substance.

The first capturing substance 1213 may include at least one among an antigen, an antibody, a modified antibody, an antibody analogue, an aptamer, nucleic acid (e.g., DNA, RNA), lipid, and a viral protein antigen.

For a more specific example, when the first target substance is an "antigen," the first capturing substance 1213 may be an antibody. Alternatively, when the first target substance is "DNA," the first capturing substance 1213 may be single stranded DNA including a sequence which is complementarily bound with a single strand of the DNA (i.e., a target substance).

The first capturing substance 1213 may be fixed to the reaction substance 1212. After the reaction substance 1212 is fixed to the magnetic nanoparticle 1211, the first capturing substance 1213 may be bound with the reaction substance 1212 to be fixed to the magnetic nanoparticle 1211.

Thus, the magnetic nanoparticle complex 1210 includes the reaction substance 1212. When the magnetic nanoparticle complex 1210 is fixed in a region adjacent to the second capturing substance 1222 on the first electrode 1220, which will be described below, the magnetic nanoparticle complex 1210 is involved in varying a detection signal in the biosensor 1000 so that it is possible to detect the presence or absence of the target substance using the biosensor 1000. The first capturing substance 1213 of the magnetic nanoparticle complex 1210 is fixed through bonding with the reaction substance 1212 and exposed to the outside of the reaction substance 1212 so that reactive degradation between the target substance and the first capturing substance 1213 may be prevented because the reaction substance 1212 is included in the magnetic nanoparticle complex 1210. A bonding degree of the reaction substance 1212 is controlled according to an exposure degree of the amine group of the magnetic nanoparticle 1211 so that an optimal magnetic nanoparticle complex 1210, in which a magnetic property of the magnetic nanoparticle complex 1210 may not be extinguished, may be implemented.

Hereinafter, a method of synthesizing the magnetic nanoparticle complex 1210 according to one embodiment of the present application will be described in detail.

1.2.1.2 Synthesis Method

Hereinafter, a method of synthesizing the magnetic nanoparticle complex 1210 using Au as a reaction substance 1212 and using an anti-prostate specific antigen (PSA) detection antibody as the first capturing substance 1213 will be described. However, Au is merely an example of the reaction substance 1212 and the anti-PSA detection antibody is merely an example of the first capturing substance 1213. It is obvious that the reaction substance 1212 may be easily replaced with another reaction substance 1212 (e.g., Ag) and the first capturing substance 1213 may be replaced with another first capturing substance 1213 (e.g., an antigen, an antibody, DNA, or the like with respect to another disease) by those skilled in the art.

In order to synthesize the magnetic nanoparticle complex 1210 according to one embodiment of the present application, 50 ml of a solution containing 1 mg of the magnetic nanoparticle 1211 having a diameter of 500 nm and modified into an amine group per 1 ml was subject to ultrasonic treatment for one hour, and then 1 ml of a solution containing 6 mg of HAuCl4.3H2O per 1 ml was added while the ultrasonic-treated solution was continuously stirred on ice for one hour.

Thereafter, 0.2 ml of 0.2 M sodium borohydride was slowly added to the solution, to which HAuCl4.3H2O was added, as a reducing agent and stirred for three hours. Then, the formed magnetic nanoparticle 1211 to which Au was fixed was washed twice with deionized water (i.e., purified water) and then stored at a temperature of 4° C. until further use.

The magnetic nanoparticle 1211, which is formed through the above procedure and to which Au was fixed, was washed twice with a phosphate buffered saline (PBS) solution. After the washing, the PBS solution was discarded, and 10 mM dithiobis (succinimidyl propionate) (DSP) dissolved in dimethyl sulfoxide (DMSO) was added to the magnetic nanoparticle, to which Au was fixed, and incubated at room temperature for thirty minutes. According to one embodiment of the present application, the DSP may serve as a linker between Au and an anti-PSA detection antibody (i.e., one example of the first capturing substance 1213) which will be added later.

Thereafter, the magnetic nanoparticle 1211, to which Au was fixed in the incubated solution, was washed with the PBS solution to remove an unbound DSP in the incubated solution. Then, an anti-PSA detection antibody was added to the magnetic nanoparticle 1211, to which Au was fixed, and incubated at room temperature for one hour and incubated at a temperature of 4° C. for sixteen hours.

The magnetic nanoparticle 1211 to which Au is fixed to which the anti-PSA antibody is fixed through the above procedure (i.e., the magnetic nanoparticle complex 1210) was washed twice with the PBS solution and stored at a temperature of 4° C. until further use.

The magnetic nanoparticle complex 1210 according to one embodiment of the present application may be synthesized through the above procedure. The magnetic nanoparticle complex 1210 is provided in the biosensor 1000 to react with the target substance included in the sample.

A detailed operation of the magnetic nanoparticle complex 1210 will be described below.

1.2.2 First Electrode 1220

1.2.2.1 Meaning

Figure 5:
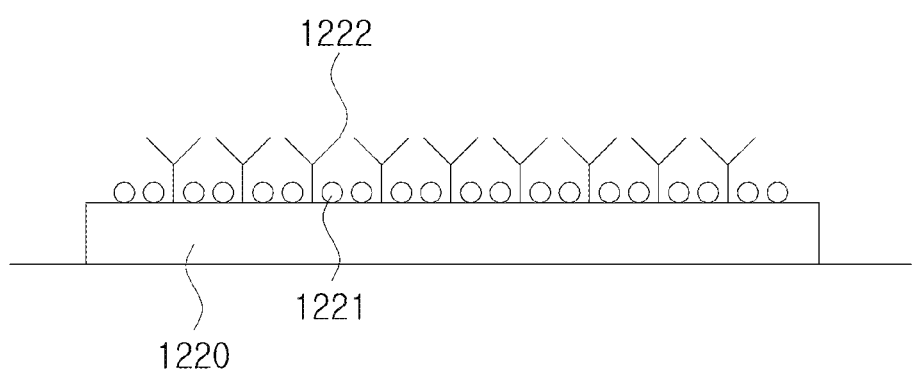
FIG. 5 is a diagram for describing a first electrode (1220) according to one embodiment of the present application.

FIG. 5 is a diagram for describing a first electrode 1220 according to one embodiment of the present application.

The first electrode 1220 is a conductive medium which emits or receives electrons and may include at least one material among materials used as electrodes in the related art, such as carbon, aluminum, platinum, Au, and/or Ag.

According to one embodiment of the present application, a blocking substance 1221 and a second capturing substance 1222 may be disposed on the first electrode 1220. Alternatively, the biosensor 1000 may also be manufactured in the form in which the blocking substance 1221 is not fixed on the first electrode 1220, the second capturing substance 1222 is not disposed thereon, or another material is further formed thereon.

The blocking substance 1221 may be a material which prevents the target substance included in the sample from being adhered into the first electrode 1220. The blocking substance 1221 may be a material which prevents the target substance included in the sample from being fixed to the first electrode 1220. The blocking substance 1221 may be a material which prevents other materials other than the target substance included in the sample (i.e., non-target substances) from being adhered into the first electrode 1220. In other words, the blocking substance 1221 may be a material which prevents the non-target substance from being fixed to the first electrode 1220. For example, the blocking substance 1221 may be a protein such as BSA (bovine serum albumin), a saccharide such as sucrose, or a detergent such as Tween-20 or Triton X-100.

The blocking substance 1221 may be disposed on the first electrode 1220. The blocking substance 1221 may be disposed in at least a portion of a region of the first electrode 1220. The blocking substance 1221 may be fixed in at least a portion of the region of the first electrode 1220.

In the biosensor 1000 including the magnetic nanoparticle complex 1210, it may be essential for the biosensor 1000 to be manufactured in the form in which the blocking substance 1221 is disposed on the first electrode 1220. In this regard, a description thereof will be made in detail below together with a result graph according to an experiment.

The second capturing substance 1222 may be a material which is specifically bound with a second target substance. For example, the second target substance may be a target substance (that is, a material to be detected, which is included in the sample). In this case, the second capturing substance 1222 may be a material which is specifically bonded to the target substance.

The second capturing substance 1222 may include at least one among an antigen, an antibody, a modified antibody, an antibody analogue, an aptamer, nucleic acid (e.g., DNA, RNA), lipid, and a viral protein antigen.

For a more specific example, when the second target substance is an "antigen," the second capturing substance 1222 may be an antibody. Alternatively, when the second target substance is "DNA," the second capturing substance 1222 may be single stranded DNA including a sequence complementarily binding to a single strand of the DNA (i.e., the target substance).

The second capturing substance 1222 may be the same material as the first capturing substance 1213. In other words, when the second capturing substance 1222 is an anti-PSA antibody, the first capturing substance 1213 may be the same anti-PSA antibody.

Alternatively, the second capturing substance 1222 may be a material different from the first capturing substance 1213. In other words, when the second capturing substance 1222 is an anti-PSA antibody, the first capturing substance 1213 may react with the PSA but may be an antibody which is specifically bound with an epitope different from an epitope with which the second capturing substance 1222 bind.

The second capturing substance 1222 may be fixed on the first electrode 1220. Thus, after the second capturing substance 1222 is fixed on the first electrode 1220, the blocking substance 1221 is fixed thereon so that the second capturing substance 1222 may not degrade improvement of the detection signal of the blocking substance 1221 in the biosensor 1000.

Hereinafter, a method of manufacturing the first electrode 1220 to which the blocking substance 1221 and the second capturing substance 1222 are fixed according to one embodiment of the present application will be described in detail.

1.2.1.2 Method of Manufacturing First Electrode 1220 to which Blocking Substance 1221 and Second Capturing Substance 1222 are Fixed Hereinafter, a method of manufacturing the first electrode 1220 to which the blocking substance 1221 and the second capturing substance 1222 are fixed, wherein BSA is used as the blocking substance 1221 and an anti-PSA detection antibody is used as the second capturing substance 1222, will be described.

However, BSA is merely an example of the blocking substance 1221 and the anti-PSA detection antibody is merely an example of the second capturing substance 1222. It is obvious that the blocking substance 1221 may be easily replaced with another blocking substance 1221 and the second capturing substance 1222 may be replaced with another second capturing substance 1222 (e.g., an antigen, an antibody, DNA, or the like with respect to another disease) by those skilled in the art.

In order to manufacture the first electrode 1220 to which the blocking substance 1221 and the second capturing substance 1222 are fixed according to one embodiment of the present application, the anti-PSA antibody may be fixed to a screen-printed carbon electrode (SPCE) through carbodiimide crosslinking.

In one method, a surface of the carbon electrode was treated with hexamethylenediamine (HMD) at room temperature for overnight to introduce an amine functional group. The carbon electrode was washed with deionized water (i.e., purified water) and then was placed in a mixed solution in which 0.4 M (1-ethyl-3-(3-dimethylaminopropyl)carbodiimide hydrochloride) (EDC), 0.1 M sulfo-(N-hydroxysulfosuccinimide) (NHS), and 0.1 mg/ml anti-PSA antibody is mixed with MES buffer (pH 4.7) and incubated in a controlled humidity chamber at room temperature for two hours.

In order to treat BSA, which is an example of the blocking substance 1221, on the electrode to which the second capturing substance 1222 (e.g., an anti-PSA antibody) was fixed generated through the above procedure, the electrode subjected to the above procedure was treated with a 1% BSA solution and slowly stirring thereof, and then the electrode was washed with a PBA solution.

Subsequently, the washed electrode, to which the blocking substance 1221 (e.g., the BSA) and the second capturing substance 1222 (e.g., the anti-PSA antibody) are fixed, is blow-dried with N2 gas and then stored at a temperature of 4° C. until further use.

Through the above-described procedure, the first electrode 1220 to which the blocking substance 1221 and the second capturing substance 1222 are fixed according to one embodiment of the present intention may be manufactured. The first electrode 1220 may be provided in the biosensor 1000 to react with a target substance included in a sample.

The first electrode 1220 to which the blocking substance 1221 and the second capturing substance 1222 are fixed according to one embodiment of the present application may serve as a working electrode in the biosensor 1000. A detailed function of the first electrode 1220 will be easily understood through a detailed embodiment described in the operation of the biosensor 1000.

1.2.3 Second Electrode 1230

The second electrode 1230 is a conductive medium which emits or receives electrons and may include at least one material among materials used as electrodes in the related art, such as carbon, aluminum, platinum, Au, and/or Ag.

The second electrode 1230 may be separately disposed from the first electrode 1220. The second electrode 1230 may be physically separated from the first electrode 1220. The second electrode 1230 may be an electrode different from the first electrode 1220.

Here, the second electrode 1230 being different from the first electrode 1220 may include a case in which material compositions constituting the first electrode 1220 and the second electrode 1230 are different from each other as well as a case in which, even when the material compositions constituting the first electrode 1220 and the second electrode 1230 are the same, there are two electrodes in which the first electrode 1220 and the second electrode 1230 are physically separated and divided.

The second electrode 1230 according to one embodiment of the present application may serve as a reference electrode in the biosensor 1000. A detailed function of the second electrode 1230 will be easily understood through a detailed embodiment described in the operation of the biosensor 1000.

Contact Part 1300

The contact part 1300 may be made of a material having electrical conductivity. For example, the contact part 1300 is a conductive medium which emits or receives electrons and may include at least one material among materials used as electrodes in the related art, such as carbon, aluminum, platinum, Au, and/or Ag.

The contact part 1300 may include a first terminal electrically connected to the first electrode 1220 and a second terminal electrically connected to the second electrode 1230. When the contact part 1300 is made of an electrode material, the contact part 1300 may include a fourth electrode electrically connected to the first electrode and a fifth electrode electrically connected to the second electrode 1230.

At least a portion of the contact part 1300 may be exposed to the outside of the biosensor 1000. For example, when the contact part 1300 includes the first terminal electrically connected to the first electrode 1220 and the second terminal electrically connected to the second electrode 1230, at least a portion of the first terminal and at least a portion of the second terminal may be exposed to the outside of the biosensor 1000. As another example, when the contact part 1300 is made of an electrode material, at least a portion of the fourth electrode electrically connected to the first electrode 1220 and at least a portion of the fifth electrode electrically connected to the second electrode 1230 may be exposed to the outside of the biosensor 1000.

According to one embodiment of the present application, the contact part 1300 may be implemented in the form in which the first electrode 1220 and the fourth electrode are formed as a single electrode and the second electrode 1230 and the fifth electrode are formed as a single electrode. Here, the first electrode 1220 and the fourth electrode being formed as a single electrode may mean a form in which one side of the single electrode is connected to the reaction part 1200 and is fixed to the second capturing substance 1222, and the other side of the single electrode is exposed to the outside of the biosensor 1000. Here, the second electrode 1230 and the fifth electrode being formed as a single electrode may mean a form in which one side of the single electrode is connected to the reaction part 1200 and the other side of the single electrode is exposed to the outside of the biosensor 1000.

The contact part 1300 may have a function of performing electrical connection to the detection device 2000 which will be described below. A region of the contact part 1300 exposed to the outside of the biosensor 1000 may have the function of performing electrical connection to the detection device 2000.

An electrical connection between the contact part 1300 and the detection device 2000 may be implemented through a physical connection. The contact part 1300 may implement the electrical connection with the detection device 2000 in the form of being inserted into the detection device 2000.

The contact part 1300 according to one embodiment of the present application is electrically connected to the detection device 2000 so that a voltage applied between the first electrode 1220 and the second electrode 1230 may be controlled through a controller 2400 of the detection device 2000. The contact part 1300 according to one embodiment of the present application is electrically connected to the detection device 2000 to allow the detection device 2000 to detect information on voltages and/or currents of the first electrode 1220 and the second electrode 1230 in the biosensor 1000.

A detailed function of the contact part 1300 according to one embodiment of the present application will be easily understood through a detailed embodiment described in the operation of the biosensor 1000.

2. Operation of Biosensor 1000

A conventionally used target detection manner of the biosensor 1000 may be broadly classified into a sandwich manner and a competitive manner.

Therefore, in the biosensor 1000 including the magnetic nanoparticle complex 1210, an operation of detecting a target substance in a sample using a sandwich manner will be described, and only a configuration and only an operation, which should be changed in an operation of detecting a target substance in a sample using a competitive manner, will be described in detail.

2.1 General Operation of Biosensor 1000

Figure 6:
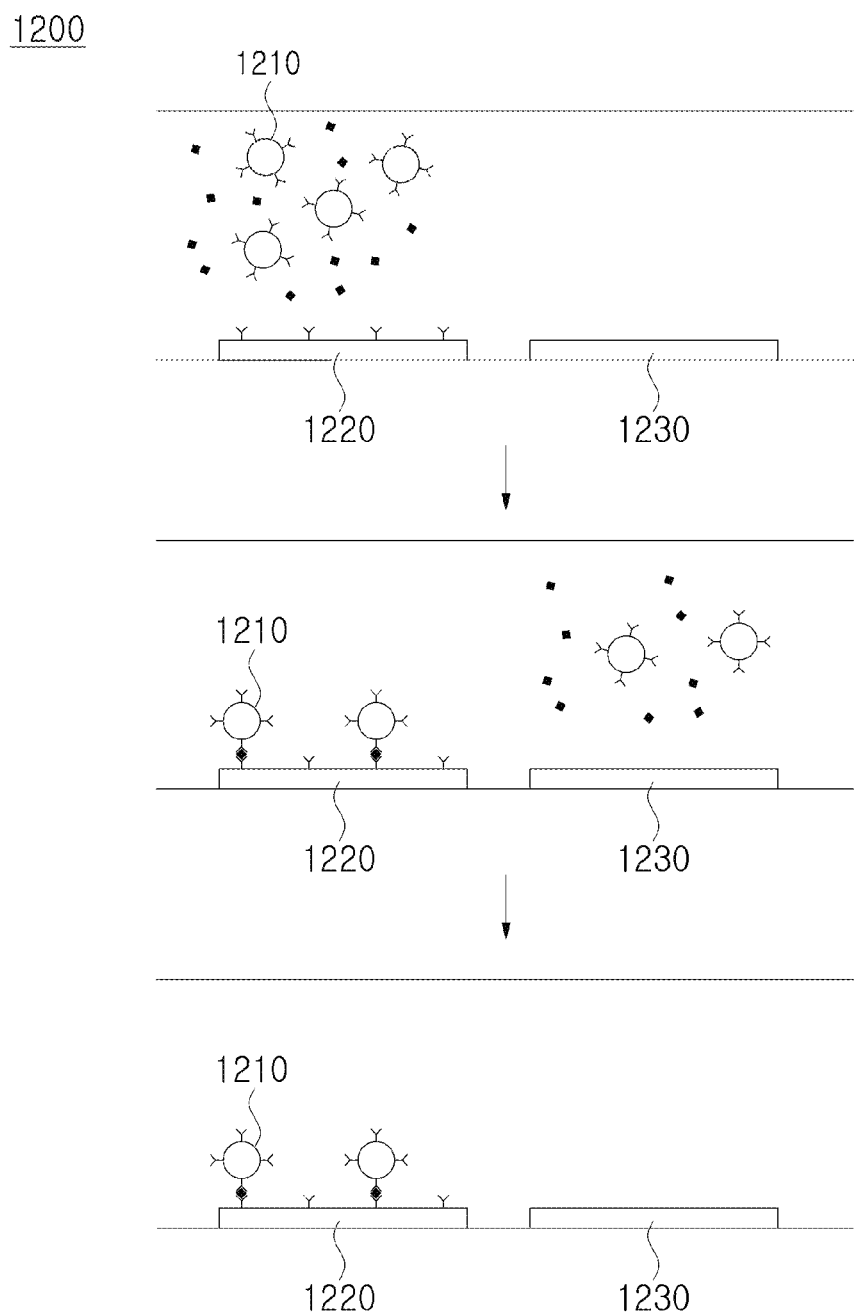
FIG. 6 is a diagram for describing a general operation of the biosensor (1000) according to one embodiment of the present application.

FIG. 6 is a diagram for describing a general operation of the biosensor 1000 according to one embodiment of the present application.

A sample may be provided to the sample introduction part 1100 of the biosensor 1000. A target substance may be included in the sample. The target substance and a non-target substance may be included in the sample. Here, the non-target substance may mean a material which is present in the sample but is not specifically bound with the first capturing substance 1213 and the second capturing substance 1222.

When the sample is provided to the sample introduction part 1100 of the biosensor 1000, the sample may move along a channel in the biosensor 1000. For example, a micro channel (or a micro fluidic channel) is formed in the biosensor 1000, and the sample provided to the sample introduction part 1100 may move due to an action of a capillary force.

The sample may pass through the sample introduction part 1100 to move to the reaction part 1200. The magnetic nanoparticle complex 1210 may be present in the reaction part 1200. As described above, the magnetic nanoparticle complex 1210 may include the magnetic nanoparticle 1211, the reaction substances 1212, and the first capturing substances 1213. The first capturing substance 1213 may be an antibody capable of specifically binding with a target substance (i.e., a first target substance). In this case, the antibody may include all of fragment type antibodies such as fragment antigen binding (Fab) including a CDR region, fragment crystallizable (Fc), and the like and/or full antibodies such as immunoglobulin G (IgG) and the like.

The target substance included in the sample moving from the sample introduction part 1100 may be specifically bound with the magnetic nanoparticle complex 1210. The target substance may be bound with the first capturing substance 1213 of the magnetic nanoparticle complex 1210. The magnetic nanoparticle complex 1210 and the target substance may perform a binding according to an antigen-antibody reaction. The antigen-antibody reaction may be performed in the reaction part 1200 of the biosensor 1000.

The first electrode 1220, to which the second capturing substance 1222 is fixed, and the second electrode 1230 may be fixed to the reaction part 1200. The magnetic nanoparticle complex 1210 bound with the target substance may be captured by the second capturing substance 1222 fixed on the first electrode 1220. In other words, the second capturing substance 1222 fixed on the first electrode 1220 may be bound with the target substance (i.e., a second target substance) bound with the magnetic nanoparticle complex 1210 and, the binding between a second capturing substance and the target substance, so, the magnetic nanoparticle complex 1210 may be captured by the second capturing substance 1222.

When the first capturing substance 1213 and the second capturing substance 1222 are antibodies, the antibody 1222 fixed on the first electrode 1220 may react with an antigen (i.e., a target substance) in the sample. The antigen bound with the antibody 1222 fixed on the first electrode 1220 may be bound with the magnetic nanoparticle complex 1210. Alternatively, antigen is bound to the antibody 1222 to which the first electrode 1220 is fixed, after bound with the antibody 1222, may be bound with the antibody 1212 of the magnetic nanoparticle complex 1210. In this case, the first target substance and the second target substance may be the same material.

When a certain period of time elapses after the sample is provided to the sample introduction part 1100, the sample excluding the magnetic nanoparticle complex 1210 and the target substance, which are captured by the second capturing substance 1222 of the first electrode 1220, may move downstream based on the reaction part 1200. The target substance, the non-target substance, and magnetic nanoparticle complex 1210, which are not captured by the first electrode 1220, may move to a sample disposal unit (not shown). A plurality of samples, which are not captured by the first electrode 1220, may be collected in the sample disposal unit.

When the magnetic nanoparticle complex 1210 is captured by the second capturing substance 1222 fixed on the first electrode 1220, a current value depending on a voltage applied to the first electrode 1220 and the second electrode 1230 (i.e., a current value output according to the applied voltage) may be changed. The current value being changed according to the voltage applied to the first electrode 1220 and the second electrode 1230 may be caused by a variation in characteristic of the material on the first electrode 1220 or the second electrode 1230 according to oxidation/reduction of the reaction substance 1212 fixed to the magnetic nanoparticle complex 1210.

According to one embodiment of the present application, the biosensor 1000 using the magnetic nanoparticle complex 1210 may be provided as a diagnostic kit of a competitive manner.

The first capturing substance 1213 of the magnetic nanoparticle complex 1210 may be an antigen. When the first capturing substance 1213 is an antigen, the first capturing substance 1213 may be bound with the second capturing substance 1222 on the first electrode 1220 in competition with the antigen (i.e., the target substance) in the sample. In this case, the first target substance captured by the first capturing substance 1213 may be the second capturing substance 1222.

The antigen (i.e., the target substance) in the sample may also be bound with the second capturing substance 1222 on the first electrode 1220. In this case, the second target substance of the second capturing substance 1222 may be the first capturing substance 1213 and the antigens in the sample.

Consequently, the first capturing substance 1213 and the antigens in the sample are competitively bound with the second capturing substance 1222 so that, as an amount of antigens in the sample increases, an amount of the first capturing substance 1213 captured by the second capturing substance 1222 on the first electrode 1220 may decrease.

When the magnetic nanoparticle complex 1210 is captured by the second capturing substance 1222 fixed on the first electrode 1220, an amount of the target substance (i.e., the antigen) captured by the second capturing substance 1222 fixed on the first electrode 1220 may decrease. Consequently, as compared with a case in which the target substance is not included in the sample, when a plurality of the target substances are included in the sample, the current value depending on the voltage applied to the first electrode 1220 and the second electrode 1230 may be detected as a small. Unlike the biosensor 1000 of the sandwich manner, when the measured detection value is small, it can be confirmed that the amount of the target substance in the sample is large.

According to another embodiment of the present application, the first capturing substance 1213 of the magnetic nanoparticle complex 1210 may be an antibody. When the first capturing substance 1213 is an antibody, the first capturing substance 1213 may be bound with the antigen (i.e., the target substance) in the sample. Alternatively, the first capturing substance 1213 may be bound with the second capturing substance 1222 on the first electrode 1220. In this case, the second capturing substance 1222 may be an antigen. The second target substance of the second capturing substance 1222 may be an antibody. In other words, the second target substance of the second capturing substance 1222 may be the first capturing substance 1213.

The antigen (i.e., the target substance) in the sample and the second capturing substance 1222 fixed to the electrode may compete for the first capturing substance 1213.

Consequently, as the antigen in the sample increases, an amount of the first capturing substance 1213 bound with the second capturing substance 1222 may decrease. As the antigen in the sample decreases, the first capturing substance 1213 bound with the second capturing substance 1222 may increase.

Consequently, as compared with a case in which the target substance is not included in the sample, when a plurality of the target substances are included in the sample, the current value depending on the voltage applied to the first electrode 1220 and the second electrode 1230 may be detected as a small value. When the measured detection value is small, it can be confirmed that the amount of the target substance in the sample is large.

2.2 Operation of Biosensor 1000 According to First Embodiment

According to one embodiment of the present application, the magnetic nanoparticle complex 1210 having a magnetic property may be provided in the reaction part 1200 of the biosensor 1000. Consequently, a state condition of the reaction part 1200 may be changed to control mobility of the magnetic nanoparticle complex 1210.

According to one embodiment of the present application, through the procedure of controlling the mobility of the magnetic nanoparticle complex 1210, other materials which are not bound with the second capturing substance 1222 on the first electrode 1220 (i.e., which are not captured by the second capturing substance 1222) may be washed.

Here, the other materials may include the target substance, the non-target substance, and the magnetic nanoparticle complex 1210 which are not captured by the first electrode 1220.

Since the magnetic nanoparticle complex 1210 which are not captured by the first electrode 1220 and the like are disposed in a region adjacent to the first electrode 1220, in order to solve a problem in that, even though the target substance is not included in the sample, a negative signal is detected and thus a false positive is diagnosed, other materials are washed by varying the state condition of the reaction part 1200 such that there is an advantage of deriving improvement in accuracy and sensitivity of the biosensor 1000 and reduction in background as effects.

A method of changing the state condition of the reaction part 1200 may include 1) changing a magnetic field formed in the reaction part 1200, 2) changing an electric field formed in the reaction part 1200, and 3) changing the magnetic field and the electric field formed in the reaction part 1200.

For example, the magnetic field formed in the reaction part 1200 may be changed by placing a magnet in a region adjacent to the first electrode 1220 and then placing the magnet in a region opposite to the first electrode. A detailed operation of the biosensor 1000 related to the above description will be described below with reference to FIG. 7.

As another example, the electric field may be changed by changing a magnitude and a frequency of a voltage applied between the first electrode 1220 and the second electrode 1230. As still another example, in the biosensor 1000 including a third electrode having a coil type different from the first electrode 1220 and the second electrode 1230, the magnetic field and/or the electric field which is formed in the reaction part 1200 may be changed by changing a current applied to the third electrode.

Figure 7:
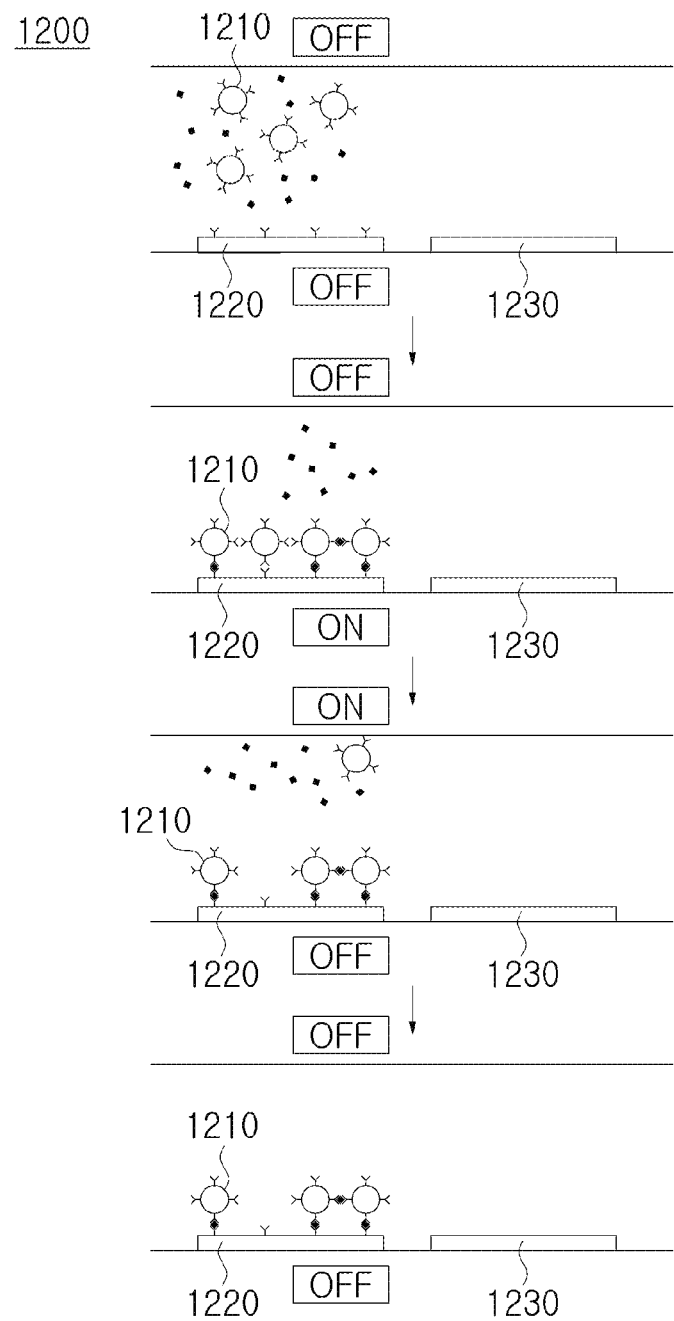
FIG. 7 is a diagram for describing an operation of a biosensor (1000) according to a first embodiment of the present application.

FIG. 7 is a diagram for describing an operation of a biosensor 1000 according to a first embodiment of the present application.

According to one embodiment of the present application, a mechanism for forming a magnetic field may be disposed at a lower end and an upper end of the first electrode 1220 of the reaction part 1200, and turning ON/OFF of the mechanism for forming a magnetic field may be controlled.

The formation of the magnetic field may also be controlled by a gap between the magnet and the first electrode 1220. When the gap between the magnet and the first electrode 1220 is small, the magnetic field in the reaction part 1200 becomes stronger. When the magnet is alternately positioned above or below the first electrode 1220, or when the turning ON/OFF of the mechanism for forming a magnetic field, which is positioned above or below, is alternately performed, movement of the magnetic nanoparticle complex 1210 is changed according to the number of times or a retention time.

More specifically, as a result of conducting an experiment using the magnetic nanoparticle complex 1210 according to one embodiment of the present application, when the magnetic nanoparticle complex 1210 is located in the reaction part 1200 and the magnet is repeatedly located upward and downward from the reaction part 1200, as compared with a case in which the magnet is repeatedly located upward and downward from the reaction part 1200 one hundred times, in a case in which the magnet is repeatedly located upward and downward from the reaction part 1200 two hundred times, a signal was slightly reduced but a relatively stable pattern was exhibited (i.e., an error bar is small). As compared with a case in which the magnet is repeatedly located upward and downward from the reaction part 1200 one or two hundred times, in a case in which the magnet is repeatedly located upward and downward from the reaction part 1200 four hundred times, it was confirmed to show a pattern in which a detection signal become larger and stable and uniformity of the detection signal was improved.

Hereinafter, for convenience of description, an operation of the biosensor 1000 will be described based on the above embodiment. However, even when an arrangement position of the mechanism for forming the magnetic field is changed or, as described above, the magnetic field and/or the electric field is changed to change an environmental condition of the reaction part 1200, the operation of the biosensor 1000 may be easily implemented by those skilled in the art, and thus a detailed description thereof will be omitted herein.

When the sample is provided to the sample introduction part 1100 of the biosensor 1000, the sample may move along a channel in the biosensor 1000.

According to another embodiment of the present application, although not required, when the sample is provided to the sample introduction part 1100 of the biosensor 1000, in order to allow environmental condition control of the reaction part 1200 to be initiated, an additional electrode different from the first electrode 1220 and the second electrode 1230 may be provided in the sample introduction part 1100 of the biosensor 1000.

The sample may pass through the sample introduction part 1100 to move to the reaction part 1200. The magnetic nanoparticle complex 1210 may be present in the reaction part 1200. When the mechanisms for generating a magnetic field positioned above or below the first electrode 1220 of the reaction part 1200 is turned off, the magnetic nanoparticle complex 1210 and the sample may move from the sample introduction part 1100 in a downstream direction.

The target substance may be bound with the first capturing substance 1213 of the magnetic nanoparticle complex 1210. The magnetic nanoparticle complex 1210 and the target substance may perform a binding according to an antigen-antibody reaction. The antigen-antibody reaction may be performed in the reaction part 1200 of the biosensor 1000.

The target substance may be bound with the second capturing substance 1222 of the first electrode 1220. The magnetic nanoparticle complex 1210 bound with the target substance which is bound with the second capturing substance 1222 may be captured by the second capturing substance 1222 to be involved in a variation in detection signal of the biosensor 1000.

According to one embodiment of the present application, when the mechanism for generating a magnetic field positioned above the first electrode 1220 of the reaction part 1200 is turned off and the mechanism for generating a magnetic field positioned below the first electrode 1220 of the reaction part 1200 is turned on, movement of the magnetic nanoparticle complex 1210 may be guided toward the first electrode 1220 of the reaction part 1200. Through the above procedure, a reaction between the target substance and the first capturing substance 1213 of the magnetic nanoparticle complex 1210 and/or between the target substance and the second capturing substance 1222 of the first electrode 1220 may be improved.

Thereafter, when the mechanism for generating a magnetic field positioned below the first electrode 1220 of the reaction part 1200 is turned off and the mechanism for generating a magnetic field positioned above the first electrode 1220 of the reaction part 1200 is turned on, the movement of the magnetic nanoparticle complex 1210 may be guided toward the upper side of the first electrode 1220 of the reaction part 1200. In such an environmental condition, a magnetic nanoparticle complex 1210 which is not captured by the second capturing substance 1222 of the first electrode 1220 is guided toward the upper side of the first electrode 1220 so that the magnetic nanoparticle complex 1210 which is not captured by a region adjacent to the second capturing substance 1222 of the first electrode 1220 may be washed. In other words, the magnetic nanoparticle complex 1210 which is not captured by the second capturing substance 1222 of the first electrode 1220 is guided toward the upper side of the first electrode 1220 so that the magnetic nanoparticle complex 1210 which is not captured by the region adjacent to the second capturing substance 1222 of the first electrode 1220 may be removed.

According to another embodiment of the present application, a first environmental condition, in which the mechanism for generating a magnetic field positioned above the first electrode 1220 of the reaction part 1200 is turned off and the mechanism for generating a magnetic field positioned below the first electrode 1220 of the reaction part 1200 is turned on, and a second environmental condition, in which the mechanism for generating the magnetic field positioned below the first electrode 1220 of the reaction part 1200 is turned off and the mechanism for generating a magnetic field positioned above the first electrode 1220 of the reaction part 1200 is turned off, may be repeatedly performed.

In other words, in addition to the embodiment in which the first environmental condition is set in the reaction part 1200, a certain period of time elapses, and then the second environmental condition is set in the reaction part 1200, it may be controlled such that the second environmental condition is set after the first environmental condition is set in the reaction part 1200, and then the first environmental condition and the second environmental condition are sequentially and repeatedly set.

Through such a procedure, a specific binding of the target substance included in the sample with the magnetic nanoparticle complex 1210 may be performed more actively. In other words, through such a procedure, an amount of the specific binding of the target substance included in the sample with the magnetic nanoparticle complex 1210 may increase. Consequently, sensitivity of the biosensor 1000 may be improved.

When the mechanism for generating a magnetic field positioned above the first electrode 1220 of the reaction part 1200 is turned off and the mechanism for generating a magnetic field positioned below the first electrode 1220 of the reaction part 1200 is turned off, the magnetic nanoparticle 1211, the non-target substance, and the target substance, which are not captured by the second capturing substance 1222, may move downstream from the reaction part 1200.

After the magnetic nanoparticle 1211, the target substance, and the non-target substance, which are not captured by the second capturing substance 1222, move to the sample disposal unit located downstream from the reaction part 1200, the presence or absence of the target substance in the sample may be confirmed by detecting a current value depending on a voltage applied to the first electrode 1220 and the second electrode 1230.

According to one embodiment of the present application, a third electrode in the form of a coil may be disposed above and below the reaction part 1200. A current applied to the third electrodes disposed above and below the reaction part 1200 is adjusted such that a magnetic field formed in the reaction part 1200 may be controlled.

Figure 8:
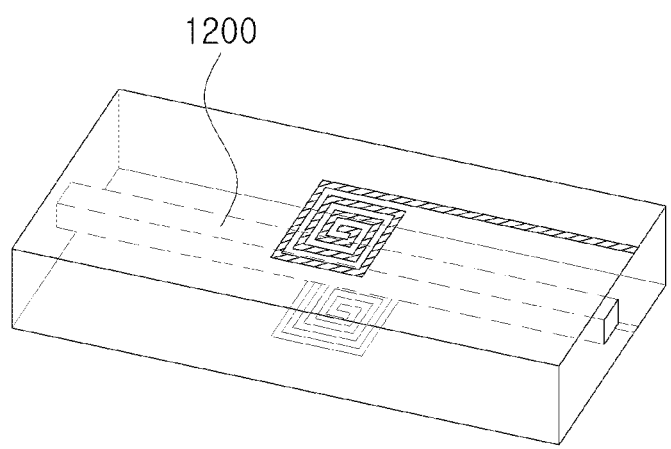
FIG. 8 is an enlarged view for describing an arrangement of a third electrode for providing a magnetic field according to one embodiment of the present application.

FIG. 8 is an enlarged view for describing an arrangement of a third electrode for providing a magnetic field according to one embodiment of the present application.

FIG. 8 is an enlarged view of the reaction part 1200 in the biosensor 1000 shown in FIG. 2.

The third electrodes in the form of a coil may be formed above and below the reaction part 1200. When the biosensor 1000 is electrically connected to the detection device 2000, a current applied to the third electrodes may be controlled.

Specifically, when a current is applied to the third electrode located above the reaction part 1200, an effect similar to that in which a magnet is disposed above the reaction part 1200 may be obtained. For example, when a current is applied to the third electrode located above the reaction part 1200, the magnetic nanoparticle complex 1210 may move to a position adjacent to the third electrode located above the reaction part 1200. In addition, when a current is applied to the third electrode located below the reaction part 1200, an effect similar to that in which a magnet is disposed below the reaction part 1200 may be obtained. For example, when a current is applied to the third electrode located below the reaction part 1200, the magnetic nanoparticle complex 1210 may move to a position adjacent to the third electrode located below the reaction part 1200.

As described above, the current applied to the third electrode disposed above the reaction part 1200 and the third electrode disposed below the reaction part 1200 is controlled such that movement of the magnetic nanoparticle complex 1210 may be controlled.

In some cases, the movement of the magnetic nanoparticle complex 1210 may be controlled in the form of repeatedly performing an operation of applying a first current to the third electrode disposed above the reaction part 1200 and applying a second current to the third electrode disposed below the reaction part 1200.

2.3 Operation of Biosensor 1000 According to Second Embodiment

A biosensor 1000 according to one embodiment of the present application may include a first electrode 1220 to which a blocking substance 1221 is fixed. More specifically, the biosensor 1000 according to one embodiment of the present application may include the first electrode 1220 to which BSA is fixed.

The BSA being fixed on the first electrode 1220, performing a blocking function of simply preventing a target substance contained in a sample from being adhered on the first electrode 1220, in addition to may perform a function of assisting an oxidation/reduction action of the reaction substance 1212 of the magnetic nanoparticle complex 1210.

Figure 9:
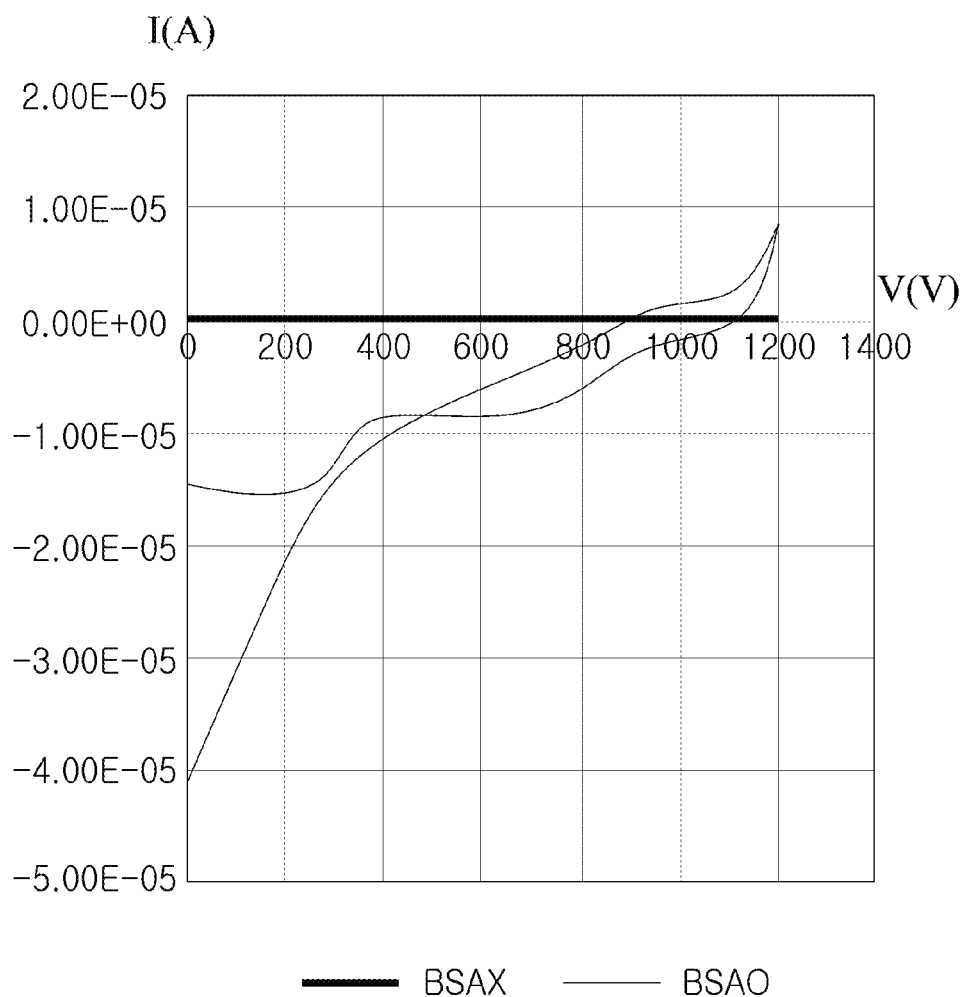
FIG. 9 is a graph for describing a variation in current over a voltage of the biosensor (1000) including a first electrode (1220) to which bovine serum albumin (BSA) is fixed according to one embodiment of the present application.

FIG. 9 is a graph for describing a variation in current over a voltage of the biosensor 1000 including the first electrode 1220 to which the BSA is fixed according to one embodiment of the present application.

Referring to FIG. 8, a sample including a target substance was provided to the biosensor 1000 including the first electrode 1220 to which the BSA was not fixed, a second capturing substance 1222 was fixed, and then detection is performed, and as a result, it was confirmed that a variation in current according to a variation in voltage was not detected (see BSAX in the illustrated graph).

However, when the BSA was fixed to the first electrode 1220 of the same biosensor 1000, the sample including the target substance was provided and detection was performed, and as a result, it was confirmed that a variation in current depending on a variation in voltage was detected (see BSAO in the illustrated graph).

Through the result graph, it was confirmed that whether the target substance is present in the sample may be detected using the biosensor 1000 including the first electrode 1220 to which the BSA and the second capturing substance 1222 are fixed, and the blocking substance 1221 (e.g., the BSA) may perform a function of assisting oxidation/reduction action in the biosensor 1000 including the magnetic nanoparticle complex 1210.

Detection Device 2000

1. Detection Device 2000

1.1. Configuration of Detection Device 2000

Figure 10:
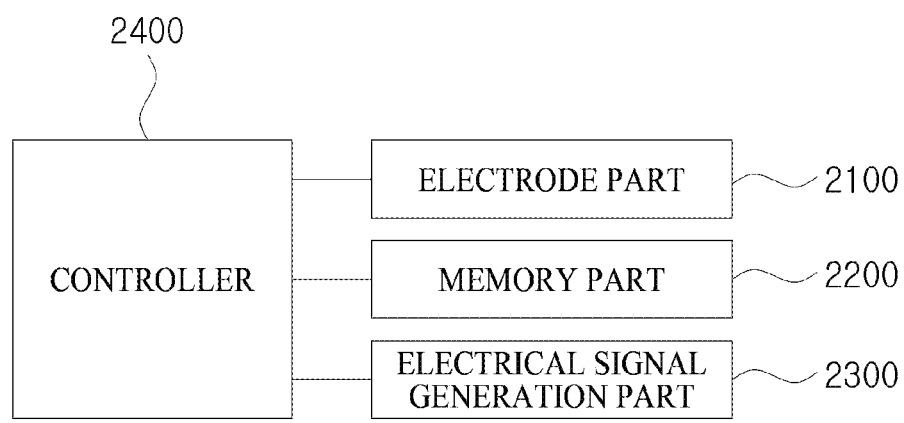
FIG. 10 is a diagram for describing a detection device (2000) according to one embodiment of the present application.

FIG. 10 is a diagram for describing a detection device 2000 according to one embodiment of the present application.

The detection device 2000 may include an electrode part 2100, a memory part 2200, an electrical signal generation part 2300, and/or a controller 2400. However, all the above components need not be included, and each component may be omitted or duplicated, and a detection device 2000 may also be manufactured in the form of further including components in addition to the above disclosed components.

1.1.1 Electrode Part 2100

The electrode part 2100 is a conductive medium which emits or receives electrons and may include at least one material among materials used as electrodes in the related art, such as carbon, aluminum, platinum, Au, and/or Ag.

The electrode part 2100 may have a function of performing electrical connection to the contact part 1300 of the biosensor 1000. The electrode part 2100 may include a first electrode terminal, which is electrically connected to the first electrode 1220 of the biosensor 1000, and a second electrode terminal which is electrically connected to the second electrode 1230 of the biosensor 1000. When the contact part 1300 of the biosensor 1000 includes a fourth electrode electrically connected to the first electrode and a fifth electrode electrically connected to the second electrode 1230, the first electrode terminal may be electrically connected to the first electrode 1220 and the fourth electrode, and the second electrode terminal may be electrically connected to the second electrode 1230 and the fifth electrode.

The electrode part 2100 according to one embodiment of the present application is electrically connected to the biosensor 1000 to allow the detection device 2000 to detect information on voltages and/or currents of the first electrode 1220 and the second electrode 1230 in the biosensor 1000.

The electrode part 2100 according to one embodiment of the present application may be electrically connected to the biosensor 1000 to perform a function of transferring electrical energy (e.g., a voltage and/or a current) generated in the detection device 2000 to the first electrode 1220 and the second electrode 1230 of the biosensor 1000.

According to one embodiment of the present application, the electrode part 2100 may be physically connected to the contact part 1300 of the biosensor 1000. The biosensor 1000 is insertion-coupled to a portion of the detection device 2000 so that the contact part 1300 of the biosensor 1000 may be in contact with the electrode part 2100 of the detection device 2000.

A function of the electrode part 2100 according to one embodiment of the present application will be easily understood through a detailed embodiment described in an operation of the detection device 2000.

1.1.2 Memory Part 2200

The memory part 2200 may perform a function of temporarily or non-temporarily storing information.

For example, the memory part 2200 may be implemented in the form of including a hard disk drive (HDD), a solid state drive (SSD), a flash memory, a read-only memory (ROM), and/or a random access memory (RAM). As another example, the memory part 2200 may be implemented in the form of being connected to another server through wireless communication to store necessary information in another server. The present disclosure is not limited thereto, and a functional unit which performs a function of storing information to allow the detection device 2000 to utilize the information may correspond to the memory part 2200 regardless of whether the functional unit has a hardware or software structure.

The memory part 2200 according to one embodiment of the present application may store information on voltage values which are to be applied to the first electrode 1220 and the second electrode 1230 of the biosensor 1000. In order to detect current values depending on voltages applied to the first electrode 1220 and the second electrode 1230 to detect whether a target substance is included in a sample introduced into the biosensor 1000, the memory part 2200 may store information on voltage values of the first electrode 1220 and the second electrodes 1230, wherein the voltage values should be applied thereto.

A function of the memory part 2200 according to one embodiment of the present application will be easily understood through a detailed embodiment described in the operation of the detection device 2000.

1.1.3 Electrical Signal Generation Part 2300

The electrical signal generation part 2300 may perform a function of generating a voltage and/or a current. For example, the electrical signal generation part 2300 may include direct current (DC) voltage/current generators. As another example, the electrical signal generation part 2300 may include a pulse width modulation (PWM) output generator. As still another example, the electrical signal generation part 2300 may include an alternating current (AC) standard voltage generator.

The electrical signal generation part 2300 may be implemented in the form of an electronic circuit such as an integrated circuit which performs a function of generating a voltage and/or a current and, alternatively, in the form of a computer or a device similar to the computer according to hardware, software, or a combination thereof. According to one embodiment of the present application, the electrical signal generation part 2300 may be implemented in the form of being included in the controller 2400.

A function of the electrical signal generation part 2300 according to one embodiment of the present application will be easily understood through a detailed embodiment described in the operation of the detection device 2000.

1.1.4 Controller 2400

The controller 2400 may control an overall operation of the detection device 2000. To this end, the controller 2400 may perform calculation and processing on various pieces of information and control operations of components of the detection device 2000.

The controller 2400 may be implemented as a computer or a device similar to the computer according to hardware, software, or a combination thereof. In terms of hardware, the controller 2400 may be provided in the form of an electronic circuit such as a central processing unit (CPU) chip which processes an electrical signal and performs a control function. In terms of software, the controller 2400 may be provided in the form of a program which drives the controller 2400 in terms of hardware.

The controller 2400 may control the electrical signal generation part 2300 to provide a voltage and/or a current to the biosensor 1000 through the electrode part 2100.

In order to detect a current depending on a variation in voltage applied to the first electrode 1220 and the second electrode 1230 of the biosensor 1000 and determine whether a target substance is captured by a sample introduced into the biosensor 1000, the controller 2400 according to one embodiment of the present application may control a voltage including a first stage of increasing a voltage applied between the first electrode 1220 and the second electrode 1230 and a second stage of decreasing the voltage to be provided. This may be to provide a circulating voltage to perform qualitative analysis and/or quantitative analysis of the target substance included in the sample.

In order to stabilize a curve of the current, the controller 2400 according to one embodiment of the present application may control a voltage, which is applied as a voltage that is higher than at least one of the lowest voltage in the first stage and the lowest voltage in the second stage for a predetermined time or more, to be provided.

Here, the stabilization means that, in a current graph according to a voltage in an operation of providing the circulating voltage, a potential/reduction potential is relatively increased when a current is maximum and/or a potential/oxidation potential value is relatively decreased when the current is minimum. Alternatively, the stabilization means that, in the current graph according to the voltage in the operation of providing the circulating voltage, a maximum current value is relatively increased and/or a minimum current value is relatively decreased. Alternatively, the stabilization means that, in the current graph according to the voltage in the operation of providing the circulating voltage, a current depending on oxidation (a current according to an increase of a voltage) corresponding to a voltage of 0 V and a current depending on reduction (a current according to a decrease of the voltage) coincide with each other relatively more.

The controller 2400 according to one embodiment of the present application may control the environmental condition of the reaction part 1200 of the biosensor 1000 to be changed through the electrode part 2100 or a separate magnetic field forming mechanism. For example, the controller 2400 controls an electrical signal provided to the first electrode 1220, the second electrode 1230, and/or the third electrode, which is electrically connected to the electrode part 2100, to change the environmental condition of the reaction part 1200 of the biosensor 1000. As another example, the controller 2400 may control turning ON/OFF of the separate magnetic forming mechanism included in the detection device 2000 to change the environmental condition of the reaction part 1200 of the biosensor 1000.

Hereinafter, unless otherwise specified, it may be construed that an operation of the detection device 2000 is performed under the control of the controller 2400. A function of the controller 2400 according to one embodiment of the present application will be easily understood through a detailed embodiment described in the operation of the detection device 2000.

1.2 Operation of Detection Device 2000

Figure 11:
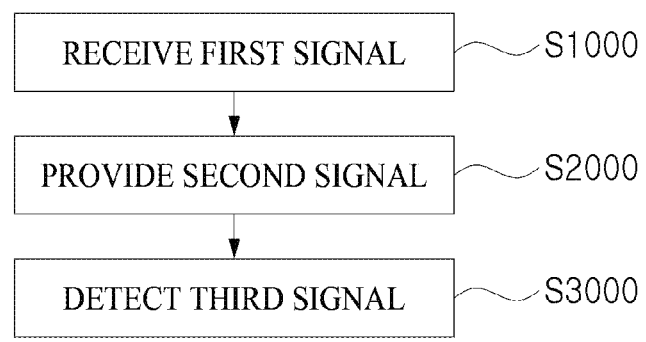
FIG. 11 is a diagram for describing an operation of the detection device (2000) according to one embodiment of the present application.

FIG. 11 is a diagram for describing an operation of the detection device 2000 according to one embodiment of the present application.

According to one embodiment of the present application, when a first signal is received (S1000), the detection device 2000 may provide a second signal (S2000) and may detect a third signal (S3000). However, each operation is not necessarily performed, and each operation may be omitted or repeated, and other procedures may be additionally performed.

1.2.1 Receiving First Signal (S1000)

According to one embodiment of the present application, the detection device 2000 may receive the first signal (S1000). For example, the first signal may mean a signal received when a sample is introduced to the sample introduction part 1100 of the biosensor 1000 through a separate electrode or the like which is additionally provided in the biosensor 1000. As another example, the first signal may mean a signal received when the sample reaches the reaction part 1200 of the biosensor 1000 through the separate electrode or the like which is additionally provided in the biosensor 1000. As still another example, the first signal may mean a signal received when the sample reaches the reaction part 1200 of the biosensor 1000 through the first electrode 1220 and/or the second electrode 1230 of the biosensor 1000. As yet another example, the first signal may mean a signal received when the sample reaches the sample disposal unit of the biosensor 1000 through the first electrode 1220 and/or the second electrode 1230 of the biosensor 1000.

When the first signal is received, the controller 2400 of the detection device 2000 may begin to provide the second signal (S2000).

1.2.2 Providing Second Signal (S2000)

According to one embodiment of the present application, the detection device 2000 may provide the second signal (S2000).

For example, the second signal may be a signal by which the detection device 2000 controls one operation of the biosensor 1000. An example of the second signal may mean 1) a signal transmitted to the biosensor 1000 so as to change the environmental condition of the reaction part 1200 of the biosensor 1000, 2) in order to determine whether the target substance is captured in the sample introduced into the biosensor 1000 by detecting a current depending on a variation in voltage applied to the first electrode 1220 and the second electrode 1230 of the biosensor 1000, a signal transmitted to the biosensor 1000 so as to provide a voltage including a first stage of increasing a voltage applied between the first electrode 1220 and the second electrode 1230 and a second stage of decreasing the voltage applied therebetween, and/or 3) in order to stabilize the curve of the current, a signal transmitted to the biosensor 1000 so as to provide a voltage which is higher than at least one of the lowest voltage in the first stage and the lowest voltage in the second stage and is applied for a predetermined time or more.

Figure 12:
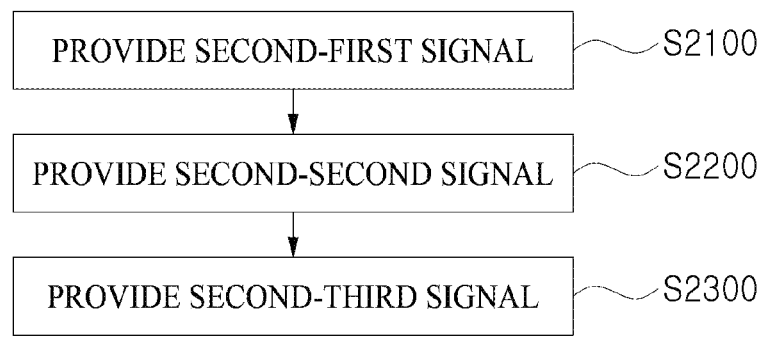
FIG. 12 is a diagram for describing an operation of providing a second signal (S2000) according to one embodiment of the present application.

FIG. 12 is a diagram for describing the provision of the second signal (S2000) according to one embodiment of the present application.

According to one embodiment of the present application, the detection device 2000 may provide a second-first signal (S2100), provide a second-second signal (S2200), and provide a second-third signal (S2300). However, each operation is not necessarily performed, and each operation may be omitted or repeated, and other procedures may be additionally performed.

The provision of the second-first signal (S2100) may mean an operation in which an electrical signal is transmitted from the detection device 2000 to the biosensor 1000 in order to change the environmental condition of the reaction part 1200 of the biosensor 1000.

For example, the controller 2400 provides an electrical signal for changing magnitudes, frequencies, and the like of the voltages applied to the first electrode 1220 and the second electrode 1230 to change the environmental condition of the reaction part 1200 of the biosensor 1000 so that movement of the magnetic nanoparticle complex 1210, the target substance, and/or the non-target substance, which are located in the reaction part 1200 of the biosensor 1000, may be changed.

As another example, the controller 2400 provides an electrical signal for changing a current applied to the coil-shaped third electrode included in the biosensor 1000 to change the environmental condition of the reaction part 1200 of the biosensor 1000 so that movement of the magnetic nanoparticle complex 1210, the target substance, and/or the non-target substance, which are located in the reaction part 1200 of the biosensor 1000, may be changed.

The provision of the second-second signal (S2200) may mean an operation in which, prior to the provision of the second-third signal (S2300), an electrical signal for applying a specific voltage is transmitted from the detection device to the biosensor 1000 so as to stabilize the curve of the current according to the provision of the second-third signal (S2300).

For example, prior to detection of the presence or absence of the target substance from the curve of the current according to the second-third signal, the provision of the second-second signal (S2200) may perform a function of inducing oxidation/reduction reactions of the magnetic nanoparticle complex 1210 captured by second capturing substance of the first electrode 1220 and stabilizing the curve of the current according to the second-third signal.

According to the provision of the second-second signal (S2200), specific voltages are applied to the first electrode 1220 and the second electrode 1230 of the biosensor 1000 for a predetermined time or more so that and the reaction substance 1212 of the magnetic nanoparticle complex 1210 undergoes oxidation pretreatment. For example, according to the provision of the second-second signal (S2200), a voltage of at least 1 V or more may be applied between the first electrode 1220 and the second electrode 1230 of the biosensor 1000 for at least two seconds. As another example, according to the provision of the second-second signal (S2200), a voltage of 1.5 V may be applied between the first electrode 1220 and the second electrode 1230 of the biosensor 1000 for ten seconds.

According to the provision of the second-second signal (S2200), specific voltages are applied to the first electrode 1220 and the second electrode 1230 of the biosensor 1000 for a predetermined time or more so that the reaction substance 1212 of the magnetic nanoparticle complex 1210 may undergo oxidation pretreatment, and then the voltage to which applied to the first electrode 1220 and the second electrode 1230 of the biosensor 1000 is decreased so that the reaction substance 1212 of the magnetic nanoparticle complex 1210 may undergo reduction pretreatment. For example, according to the provision of the second-second signal (S2200), a voltage of at least 1 V or more is applied between the first electrode 1220 and the second electrode 1230 of the biosensor 1000 for at least two seconds, and then a voltage which decreases the voltage between the first electrode 1220 and the second electrode 1230 from at least 1 V or more to at least 0 V or less may be applied. As another example, according to the provision of the second-second signal (S2200), a voltage of 1.5 V is applied between the first electrode 1220 and the second electrode 1230 of the biosensor 1000 for ten seconds, and then the voltage applied to the first electrode 1220 and the second electrode 1230 may be decreased from 1.5 V to −0.2 V at a rate of −0.1 V/s.

According to the provision of the second-second signal (S2200), the specific voltages are applied to the first electrode 1220 and the second electrode 1230 of the biosensor 1000 for a predetermined time or more so that the reaction substance 1212 of the magnetic nanoparticle complex 1210 may undergo oxidation pretreatment, and then the voltages to which applied to the first electrode 1220 and the second electrode 1230 of the biosensor 1000 are decreased so that the reaction substance 1212 of the magnetic nanoparticle complex 1210 may undergo reduction pretreatment. Thereafter, the voltages to which applied to the first electrode 1220 and the second electrode 1230 of the biosensor 1000 are increased so that the reaction substance 1212 of the magnetic nanoparticle complex 1210 may undergo oxidation pretreatment. For example, according to the provision of the second-second signal (S2200), the voltage of at least 1 V or more is applied between the first electrode 1220 and the second electrode 1230 of the biosensor 1000 for at least two seconds, and then the voltage which decreases the voltage between the first electrode 1220 and the second electrode 1230 from at least 1 V or more to at least 0 V or less may be applied. Thereafter, a voltage which increases the voltage between the first electrode 1220 and the second electrode 1230 from at least 0 V to at least 1 V may be applied. As another example, according to the provision of the second-second signal (S2200), the voltage of 1.5 V is applied between the first electrode 1220 and the second electrode 1230 of the biosensor 1000 for ten seconds, and then the voltages applied to the first electrode 1220 and the second electrode 1230 may be decreased from 1.5 V to −0.2 V at a rate of −0.1 V/s. Thereafter, the voltages applied to the first electrode 1220 and the second electrode 1230 may be increased from −0.2 V to 1.5 V at a rate of 0.1 V/s.

The provision of the second-third signal (S2300) may mean an operation in which, in order to determine whether the target substance is captured by the sample introduced into the biosensor 1000 by detecting a current according to a variation in voltage applied to the first electrode 1220 and the second electrode 1230 of the biosensor 1000, a signal for providing a voltage including a first stage of increasing a voltage applied between the first electrode 1220 and the second electrode 1230 and a second stage of decreasing the voltage applied therebetween is transmitted from the detection device to the biosensor 1000.

Figure 13:
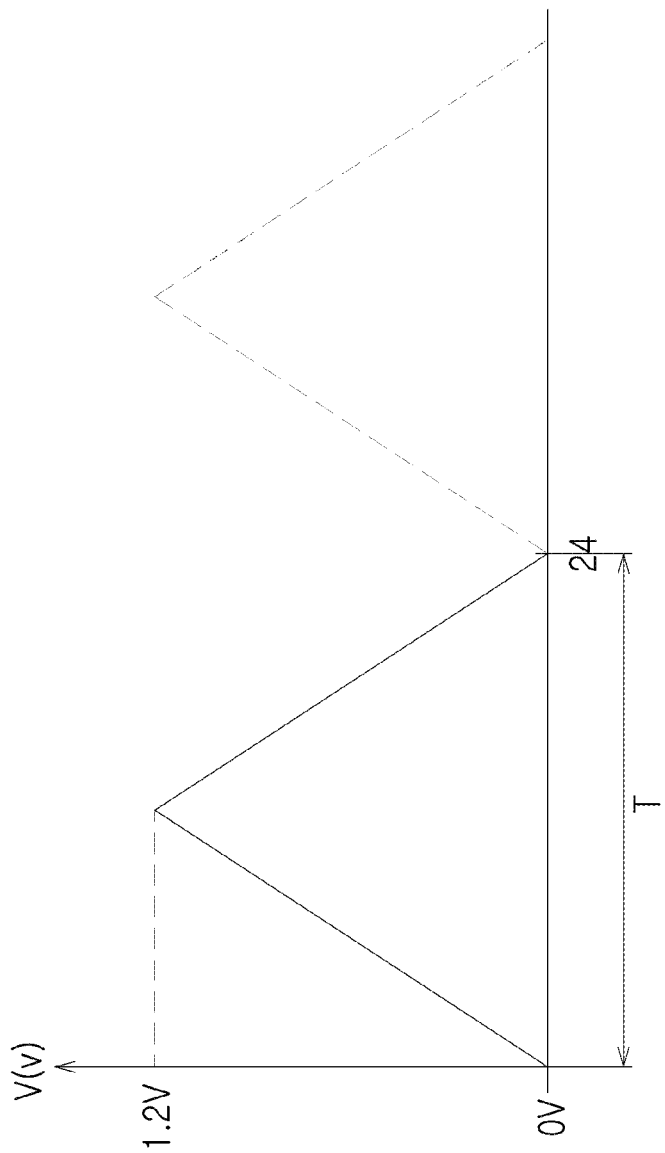
FIG. 13 is a diagram for describing an operation of providing a second-third signal (S2300) according to one embodiment of the present application.

FIG. 13 is a diagram for describing the provision of the second-third signal (S2300) according to one embodiment of the present application.

For example, in order to perform analysis on whether the target substance is included in the sample (qualitative analysis) and/or a relative amount of the target substance included in the sample (quantitative analysis) using cyclic voltammetry, the provision of the second-third signal (S2300) may perform a function of providing a switching voltage including a rising potential and a falling potential of a voltage during at least one period T.

According to the provision of the second-third signal (S2300), the voltages applied to the first electrode 1220 and the second electrode 1230 of the biosensor 1000 are increased and then decreased so that the detection device 2000 may acquire a detection value depending on oxidation of the reaction substance 1212 of the magnetic nanoparticle complex 1210 and acquire a detection value depending on reduction of the reaction substance 1212 of the magnetic nanoparticle complex 1210. For example, according to the provision of the second-third signal (S2300), a voltage which increases the voltage between the first electrode 1220 and the second electrode 1230 of the biosensor 1000 from at least 0 V or less to at least 1 V or more may be applied, and then a voltage which decreases the voltage between the first electrode 1220 and the second electrode 1230 from at least 1 V or more to at least 0 V or less may be applied. As another example, according to the provision of the second-third signal (S2300), the voltages applied to the first electrode 1220 and the second electrode 1230 of the biosensor 1000 may be increased from 0.0 V to 1.2 V at a rate of 0.1 V/s and, subsequently, the voltages applied to the first electrode 1220 and the second electrode 1230 may be decreased from 1.2 V to 0.0 V at a rate of −0.1 V/s.

According to the provision of the second-third signal (S2300), the voltages applied to the first electrode 1220 and the second electrode 1230 of the biosensor 1000 are decreased and then increased so that the detection device 2000 may acquire a detection value according to reduction of the reaction substance 1212 of the magnetic nanoparticle complex 1210 and acquire a detection value depending on oxidation of the reaction substance 1212 of the magnetic nanoparticle complex 1210. For example, according to the provision of the second-third signal (S2300), a voltage which decreases the voltage between the first electrode 1220 and the second electrode 1230 of the biosensor 1000 from at least 1 V or more to at least 0 V or less may be applied and, subsequently, a voltage which increases the voltage between the first electrode 1220 and the second electrode 1230 from at least 0 V or less to at least 1 V or more may be applied. As another example, according to the provision of the second-third signal (S2300), the voltages applied to the first electrode 1220 and the second electrode 1230 of the biosensor 1000 may be decreased from 1.2 V to 0.0 V at a rate of −0.1 V/s and, subsequently, the voltages applied to the first electrode 1220 and the second electrode 1230 may be increased from 0.0 V to 1.2 V at a rate of 0.1 V/s.

1.2.3 Detecting Third Signal (S3000)

According to one embodiment of the present application, the detection device 2000 may detect the third signal (S3000). For example, the detection of the third signal may mean an operation in which the detection device 2000 detects the currents of the first electrode 1220 and the second electrode 1230 of the biosensor 1000 according to the provision of the second-third signal (S2300).

More specifically, when the provision of the second-third signal (S2300) is to analyze the presence or absence of the target substance using cyclic voltammetry, a current graph according to the rising potential and the falling potential of the first electrode 1220 and the second electrode 1230, which are acquired from the detection of the third signal due to the provision of the second-third signal (S2300), is confirmed to have a maximum current value and a minimum current value so that it is possible to determine the presence of the target substance in the sample.

1.3 Operation of Detection Device 2000 According to Third Embodiment

Figure 14:
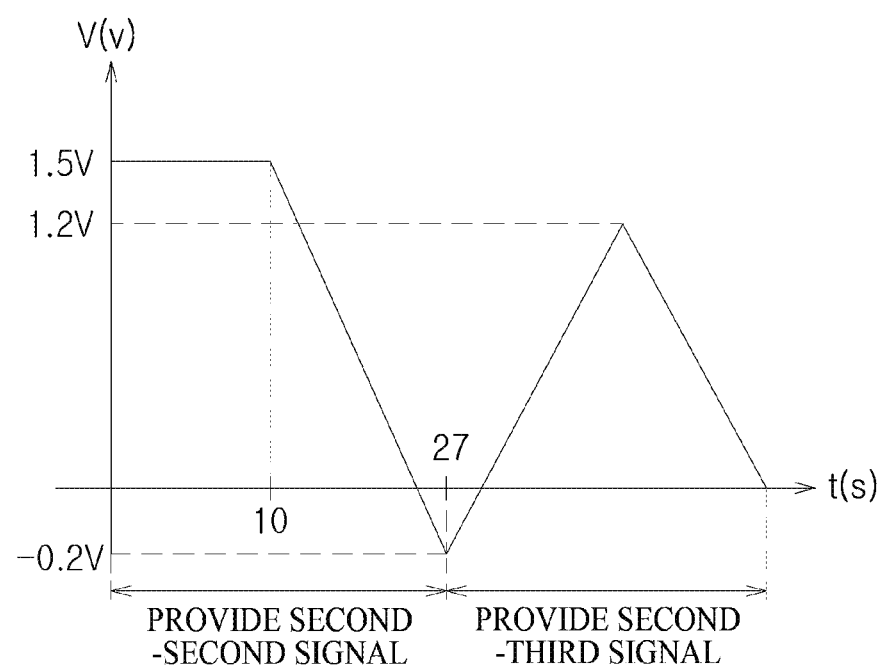
FIG. 14 is a diagram for describing an operation of performing a reduction pretreatment prior to the operation of providing of the second-third signal (S2300) according to a third embodiment of the present application.

FIG. 14 is a diagram for describing an operation of performing a reduction pretreatment prior to the provision of the second-third signal (S2300) according to a third embodiment of the present application.

The detection device 2000 according to one embodiment of the present application may operate such that the voltages applied to the first electrode 1220 and the second electrode 1230 of the biosensor 1000 according to the provision of the second-third signal (S2300) are increased from 0.0 V to 1.2 V at a rate of 0.1 V/s and, subsequently, when the second-third signal is provided such that the voltages applied to the first electrode 1220 and the second electrode 1230 are decreased from 1.2 V to 0.0 V at a rate of −0.1 V/s, the reaction part 1200 of the biosensor 1000 undergoes reduction pretreatment prior to the provision of the second-third signal (S2300).

Prior to the provision of the second-third signal (S2300), the provision of the second-second signal (S2200) may be performed such that the reaction part 1200 of the biosensor 1000 undergoes reduction pretreatment.

The detection device 2000 according to one embodiment of the present application may operate such that a voltage of 1.5 V is applied to the first electrode 1220 and the second electrode 1230 of the biosensor 1000 for ten seconds according to the provision of the second-second signal and, subsequently, the voltage applied to the first electrode 1220 and the second electrode 1230 is decreased from 1.5 V to −0.2 V at a rate of −0.1 V/s.

Figure 15:
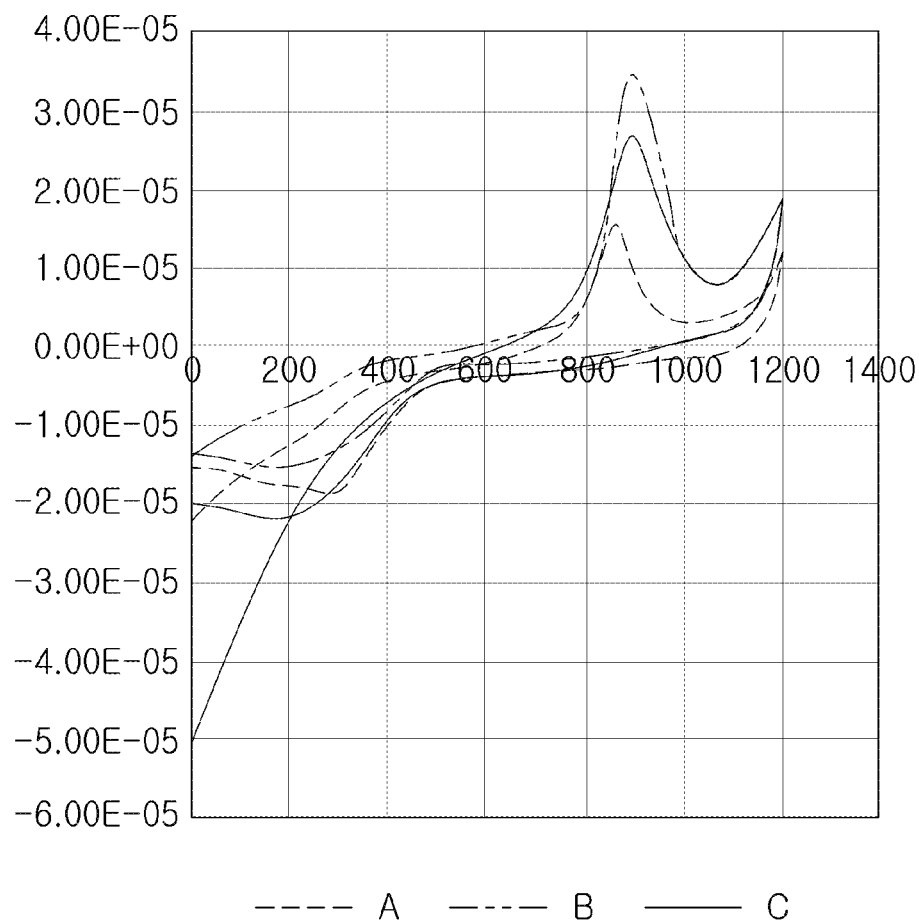
FIG. 15 is a diagram for describing a detection graph of a third signal according to an operation of providing a second-second signal (S2200) and the operation of providing of the second-third signal (S2300) according to one embodiment of the present application.

FIG. 15 is a diagram for describing a detection graph of a third signal according to the provision of the second-second signal (S2200) and the provision of the second-third signal (S2300) according to one embodiment of the present application.

Line A of FIG. 15 shows a current graph according to a voltage due to the second-third signal when the voltages applied to the first electrode 1220 and the second electrode 1230 of the biosensor 1000 are increased from 0.0 V to 1.2 V at a rate of 0.1 V/s according to the provision of the second-third signal (S2300), and when the second-third signal is provided such that the voltages applied to the first electrode 1220 and the second electrode 1230 are decreased from 1.2 V to 0.0 V at a rate of −0.1 V/s, prior to the provision of the second-third signal (S2300), voltages of 1.5 V are applied to the first electrode 1220 and the second electrode 1230 of the biosensor 1000 for ten seconds according to the provision of the second-second signal (S2200), and the voltages applied to the first electrode 1220 and the second electrode 1230 are decreased from 1.5 V to −0.2 V at a rate of −0.1 V/s and then increased from −0.2 V to 1.5 V at a rate of 0.1 V/s.

Line B of FIG. 15 shows a current graph according to the voltage due to the second-third signal when the voltages corresponding to the voltage graph over time shown in FIG. 13 are applied to the first electrode 1220 and the second electrode 1230.

Line C of FIG. 15 shows a current graph according to the voltage due to the second-third signal when the voltages applied to the first electrode 1220 and the second electrode 1230 of the biosensor 1000 are increased from 0.0 V to 1.2 V at a rate of 0.1 V/s according to the provision of the second-third signal (S2300), and when the second-third signal is provided such that the voltages applied to the first electrode 1220 and the second electrode 1230 are decreased from 1.2 V to 0.0 V at a rate of −0.1 V/s, prior to the provision of the second-third signal (S2300), voltages of 1.5 V are applied to the first electrode 1220 and the second electrode 1230 of the biosensor 1000 for ten seconds according to the provision of the second-second signal (S2200).

Referring to FIG. 15, it can be confirmed that a maximum current value in a voltage-current graph corresponding to line B was increased as compared with maximum current value in voltage-current graphs corresponding to line A and maximum current value in voltage-current graphs corresponding to line C.

In addition, referring to FIG. 15, it can be confirmed that a potential/reduction potential when the current is maximum in the voltage-current graph corresponding to line B was increased as compared with potential/reduction potential when the current is maximum in the voltage-current graph corresponding to line A and potential/reduction potential when the current is maximum in the voltage-current graph corresponding to line C.

Further, referring to FIG. 15, it can be confirmed that a current due to oxidation and a current due to reduction, which correspond to a voltage of 0 V in the voltage-current graph corresponding to line B, further coincide with each other relatively, compared with to the voltage-current graphs corresponding to lines A and C.

1.4 Operation of Detection Device 2000 According to Fourth Embodiment

In the operation of the detection device 2000 according to the third embodiment, when the current due to oxidation was detected and then the current due to the reduction was detected according to the second-third signal, and the reduction pretreatment was performed prior to the provision of the second-third signal, it was confirmed that the detected value depending on the second-third signal was stabilized.

In an operation of the detection device 2000 according to the fourth embodiment, when a current due to reduction is detected and then the current due to the oxidation is detected according to the second-third signal, an example in which oxidation pretreatment is performed so as to acquire a detected value depending on the stabilized second-third signal will be described.

Figure 16:
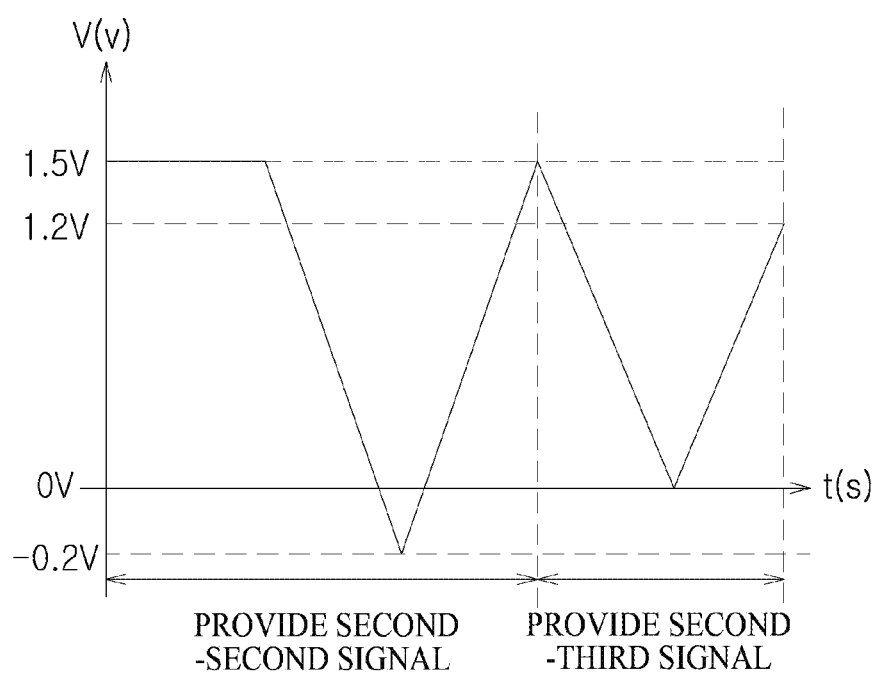
FIG. 16 is a diagram for describing an operation of performing oxidation pretreatment prior to the operation of providing of the second-third signal (S2300) according to a fourth embodiment of the present application.

FIG. 16 is a diagram for describing an operation of performing oxidation pretreatment prior to the provision of the second-third signal (S2300) according to the fourth embodiment of the present application.

The detection device 2000 according to one embodiment of the present application may operate such that the voltages applied to the first electrode 1220 and the second electrode 1230 of the biosensor 1000 are decreased from 1.2 V to 0.0 V at a rate of −0.1 V/s according to the provision of the second-third signal (S2300) and, subsequently, when the second-third signal (S2300) is provided such that the voltages applied to the first electrode 1220 and the second electrode 1230 are increased from 0.0 V to 1.2 V at a rate of 0.1 V/s, the reaction part 1200 of the biosensor 1000 undergoes reduction pretreatment prior to the provision of the second-third signal (S2300).

Prior to the provision of the second-third signal (S2300), the provision of the second-second signal (S2200) may be performed such that the reaction part 1200 of the biosensor 1000 undergoes oxidation pretreatment.

The detection device 2000 according to one embodiment of the present application may operate such that a voltage of 1.5 V may be applied to the first electrode 1220 and the second electrode 1230 of the biosensor 1000 for ten seconds according to the provision of the second-second signal (S2200).

The detection device 2000 according to one embodiment of the present application may operate such that the voltage of 1.5 V is applied to the first electrode 1220 and the second electrode 1230 of the biosensor 1000 for ten seconds according to the provision of the second-second signal (S2200) and, subsequently, the voltage applied to the first electrode 1220 and the second electrode 1230 may be decreased from 1.5 V to −0.2 V at a rate of −0.1 V/s and then increased from −0.2 V to 1.5 V at a rate of 0.1 V/s.

The detection device 2000 according to one embodiment of the present application may operate such that the voltage of 1.5 V is applied to the first electrode 1220 and the second electrode 1230 of the biosensor 1000 for ten seconds according to the provision of the second-second signal (S220) and, subsequently, the voltage applied to the first electrode 1220 and the second electrode 1230 is increased from −0.2 V to 1.5 V at a rate of 0.1 V/s.

Consequently, when the voltage applied to the first electrode 1220 and the second electrode 1230 of the biosensor 1000 is increased from 0.0 V to 1.2 V at a rate of 0.1 V/s according to the provision of the second-third signal (S2300), and then when the second-third signal is provided (S2300) such that the voltage applied to the first electrode 1220 and the second electrode 1230 is decreased from 1.2 V to 0.0 V at a rate of −0.1 V/s, as in the graph shown in FIG. 15, the most stabilized current graph according to the voltage due to the second-third signal may be acquired.

As described above, the method of analyzing the presence or absence of the target substance using cyclic voltammetry according to some embodiments of the present application has been disclosed in detail. However, according to one embodiment of the present application, it is also possible to analyze the presence or absence of the target substance using differential pulse voltammetry.

For a specific example, in the provision of the second-third signal (S2300) and the detection of the third signal (S3000), a pulse signal may be provided at a time of the provision of the second-third signal (S2300) in the form of a voltage having 1) a step potential of 4 mV in a range of 1 v to 0 V, 2) a modulation amplitude of −50 mV, 3) a modulation time of 5 seconds, and 4) an interval time of 200 ms.

Consequently, in the detection of the third signal (S3000), a graph of a current depending on an applied pulse may be illustrated, and whether the illustrated graph has a maximum current value or a minimum current value is determined so that the presence of the target substance in the sample may be determined.

As described above, although a configuration and a feature of the present application have been described on the basis of the embodiments according to the present application, the present application is not limited thereto, and it is apparent to those skilled in the art that various alternations or modifications can be made within the spirit and scope of the present application. Therefore, it is noted that these alternations or modifications fall within the scope of the appended claims.

What is claimed is:

1. A biosensor used to detect whether a target substance is included in a sample based on a change of a current in response to a change of a voltage applied between a first electrode and a second electrode, the biosensor comprising:
    a reaction part including a magnetic nanoparticle complex, the first electrode, and the second electrode; and
    a sample introduction part forming a passage so that the sample can be introduced into the reaction part from an outside of the biosensor;
    wherein the magnetic nanoparticle complex includes a magnetic nanoparticle, and a reaction substance is fixed to the magnetic nanoparticle, and a first capturing substance is fixed to the reaction substance,
    wherein the first capturing substance is configured to capture the target substance or is configured to capture a second capturing substance,
    wherein the reaction substance performs at least one reaction selected from an oxidation reaction and a reduction reaction,
    wherein the magnetic nanoparticle complex is magnetic in the reaction part, and has a property that a movement of the magnetic nanoparticle complex is changed according to a change in a condition of the reaction part,
    wherein the second capturing substance is configured to capture the target substance, and is fixed to the first electrode,
    wherein the second electrode is an electrode different from the first electrode, and
    wherein, when the first capturing substance of the magnetic nanoparticle complex is captured by the second capturing substance of the first electrode directly or indirectly, the reaction of the reaction substance induces the change of the current in response to a voltage change applied between the first electrode and the second electrode to represent existence of the target substance included in the sample.

2. The biosensor of claim 1, wherein the reaction substance is fixed to a reactor formed on a surface of the magnetic nanoparticle.

3. The biosensor of claim 2, wherein the reactor is an amine, and the reaction substance is gold.

4. The biosensor of claim 1, wherein a blocking substance that prevents adhesion of the target substance is located on of at least a portion of the first electrode.

5. The biosensor of claim 4, wherein the blocking substance is a BSA (Bovine Serum Albumin).

6. The biosensor of claim 1, wherein the first capturing substance includes at least one selected from an antigen, an antibody, a modified antibody, an antibody analog, an aptamer, a nucleic acid, a lipid, and a viral protein antigen, and wherein the second capturing substance includes at least one of an antigen, an antibody, a modified antibody, an antibody analog, an aptamer, a nucleic acid, a lipid, and a viral protein antigen.

7. The biosensor of claim 1, wherein the first capturing substance is an antibody, the target substance is an antigen interacting with the first capturing substance, the second capturing substance is same substance with the first capturing substance, wherein when the target substance is included in the sample, the second capturing substance bonds to the target substance and the target substance bonds to the first capturing substance such that the first capturing substance is captured by the second capturing substance indirectly.

8. The biosensor of claim 1, wherein the first capturing substance is an antigen, the second capturing substance is an antibody interacting with the first capturing substance, the target substance is same substance with the first capturing substance, wherein when the target substance is included in the sample, the second capturing substance bonds to the first capturing substance competitively with the target substance such that the first capturing substance is captured by the second capturing substance directly.

9. The biosensor of claim 1, wherein the first capturing substance is an antigen, the target substance is an antibody interacting with the first capturing substance, the second capturing substance is same substance with the first capturing substance, wherein when the target substance is included in the sample, the second capturing substance bonds to the target substance and the target substance bonds to the first capturing substance such that the first capturing substance is captured by the second capturing substance indirectly.

10. The biosensor of claim 1, when a magnetic field formed in the reaction part is changed, wherein a direction of the movement of the magnetic nanoparticle complex is changed.

11. The biosensor of claim 1, when the voltage applied between the first electrode and the second electrode is changed, wherein a direction of the movement of the magnetic nanoparticle complex is changed.

12. The biosensor of claim 1, further comprising a third electrode having a coil shape different from the first electrode and the second electrode, and when a current applied to the third electrode is changed, wherein a direction of the movement of the magnetic nanoparticle complex is changed.

13. The biosensor of claim 1, wherein at least a portion of a fourth electrode electrically connected to the first electrode and at least a portion of a fifth electrode electrically connected to the second electrode are exposed to the outside of the biosensor.

14. The biosensor of claim 13, wherein the first electrode and the fourth electrode are composed of one electrode, and wherein the second electrode and the fifth electrode are composed of one electrode.

15. The biosensor of claim 13, wherein at least a portion of the fourth electrode and at least a portion of the fifth electrode are electrically connected to a device capable of measuring a current.

16. The biosensor of claim 15, wherein the voltage applied between the first electrode and the second electrode is controlled by the device.

17. The biosensor of claim 1, wherein the first capturing substance is an antibody, the second capturing substance is an antigen interacting with the first capturing substance, the target substance is same substance with the first capturing substance, wherein when the target substance is included in the sample, the second capturing substance bonds to the first capturing substance competitively with the target substance such that the first capturing substance is captured by the second capturing substance directly.

* * * * *

UNITED STATES PATENT AND TRADEMARK OFFICE
CERTIFICATE OF CORRECTION

| | | |
|---|---|---|
| PATENT NO. | : 11,041,854 B2 | Page 1 of 1 |
| APPLICATION NO. | : 17/002632 | |
| DATED | : June 22, 2021 | |
| INVENTOR(S) | : Hyundoo Hwang and Jaekyu Choi | |

It is certified that error appears in the above-identified patent and that said Letters Patent is hereby corrected as shown below:

On the Title Page

In Column 2, item (57), ABSTRACT, Line 11, delete "has is" and insert --is--.

In the Specification

In Column 5 at Line 7, delete "provided" and insert --provided.--.

In Column 5 at Line 31, delete "provided" and insert --provided.--.

In Column 10 at Line 26, delete "MnFe2O4))," and insert --MnFe2O4),--.

In the Claims

In Column 33 at Line 3, Claim 4, delete "of at" and insert --at--.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*